(12) United States Patent
Ojha

(10) Patent No.: US 10,010,271 B2
(45) Date of Patent: Jul. 3, 2018

(54) METHOD AND APPARATUS FOR MONITORING AND REPORTING ON THE STATUS OF AN OCCUPANT OF AN OCCUPANT SUPPORT

(71) Applicant: Hill-Rom Services, Inc., Batesville, IN (US)

(72) Inventor: Unnati Ojha, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 15/459,212

(22) Filed: Mar. 15, 2017

(65) Prior Publication Data

US 2017/0296103 A1      Oct. 19, 2017

Related U.S. Application Data

(60) Provisional application No. 62/322,924, filed on Apr. 15, 2016.

(51) Int. Cl.
  *G08B 23/00*  (2006.01)
  *A61B 5/11*   (2006.01)
  (Continued)

(52) U.S. Cl.
  CPC .......... *A61B 5/1116* (2013.01); *A47G 9/1045* (2013.01); *A61B 5/6892* (2013.01);
  (Continued)

(58) Field of Classification Search
  CPC ....... A61B 5/1116; A61B 5/11; A61B 5/1115; A61B 5/1118; A61B 5/1071; G08B 21/0446
  (Continued)

(56) References Cited

U.S. PATENT DOCUMENTS

| 6,208,250 B1 | 3/2001 | Dixon et al. |
| 7,524,278 B2 | 4/2009 | Auphan |

(Continued)

FOREIGN PATENT DOCUMENTS

| CN | 202112763 U  | 1/2012 |
| CN | 103006227 A  | 4/2013 |

(Continued)

OTHER PUBLICATIONS

Washington University Graduates Create Smart Pillow to Improve Sleep Quality—Article; Kyle Loethen; May 27, 2015; Ultradia Co-Founder and CEO Zimin Hang.

(Continued)

*Primary Examiner* — Toan N Pham
(74) *Attorney, Agent, or Firm* — Kenneth C. Baran

(57) ABSTRACT

A method for monitoring an occupant of an occupant support comprises 1) establishing a lateral position history of the occupant, which history includes an assessment of how frequently the occupant's head undergoes a lateral transition on a head support, 2) establishing a vertical position history of the occupant which accounts for how frequently the weight of the occupant's head is applied to and removed from the head support, and 3) if the lateral position history indicates sustained repetitive lateral movement or the vertical history indicates other than sustained presence of the occupant's head on the head support, reporting that the occupant is in a state other than an acceptable state.

23 Claims, 23 Drawing Sheets

US 10,010,271 B2
Page 2

(51) Int. Cl.
*A61G 7/07* (2006.01)
*A47G 9/10* (2006.01)
*A61B 5/00* (2006.01)
*G08B 21/04* (2006.01)
*G16H 15/00* (2018.01)
*A61G 7/05* (2006.01)

(52) U.S. Cl.
CPC ............ *A61B 5/72* (2013.01); *A61G 7/072* (2013.01); *G08B 21/0461* (2013.01); *G16H 15/00* (2018.01); *A61B 5/6891* (2013.01); *A61B 2562/0247* (2013.01); *A61B 2562/0252* (2013.01); *A61B 2562/043* (2013.01); *A61G 7/0527* (2016.11)

(58) Field of Classification Search
USPC ...... 340/573.1, 506, 517, 539.12, 686.1, 3.1
See application file for complete search history.

(56) References Cited

U.S. PATENT DOCUMENTS

| | | | |
|---|---|---|---|
| 9,295,390 B2 | 3/2016 | Receveur et al. | |
| 9,836,942 B2* | 12/2017 | Wiggermann | G08B 21/0446 |
| 2011/0068928 A1* | 3/2011 | Riley | A61B 5/02055 340/573.1 |
| 2013/0317399 A1* | 11/2013 | Ribble | G06F 19/3431 601/84 |
| 2016/0128610 A1* | 5/2016 | Kostic | A61B 5/1115 5/613 |

FOREIGN PATENT DOCUMENTS

| | | |
|---|---|---|
| CN | 203736193 U | 7/2014 |
| NL | 8701288 A | 1/1989 |
| WO | 2008139500 A1 | 11/2008 |
| WO | 2014114438 A1 | 7/2014 |
| WO | 2015033008 A1 | 3/2015 |

OTHER PUBLICATIONS

EE Times—Inside the Measurement Pillow; Blog—Martin Rowe, Senior Technical Editor, Mar. 24, 2015; Printed from Internet Feb. 4, 2016.

* cited by examiner

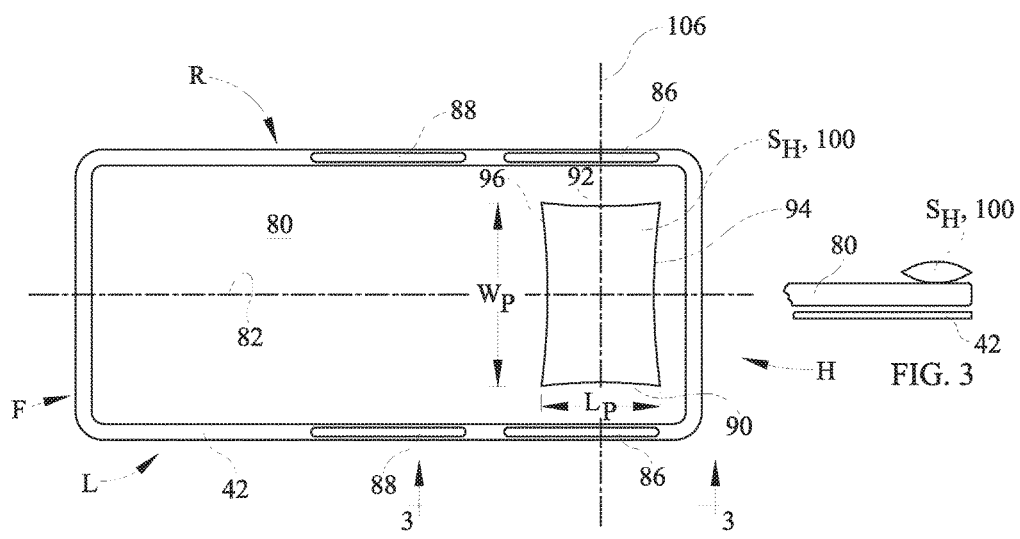
FIG. 2
FIG. 3
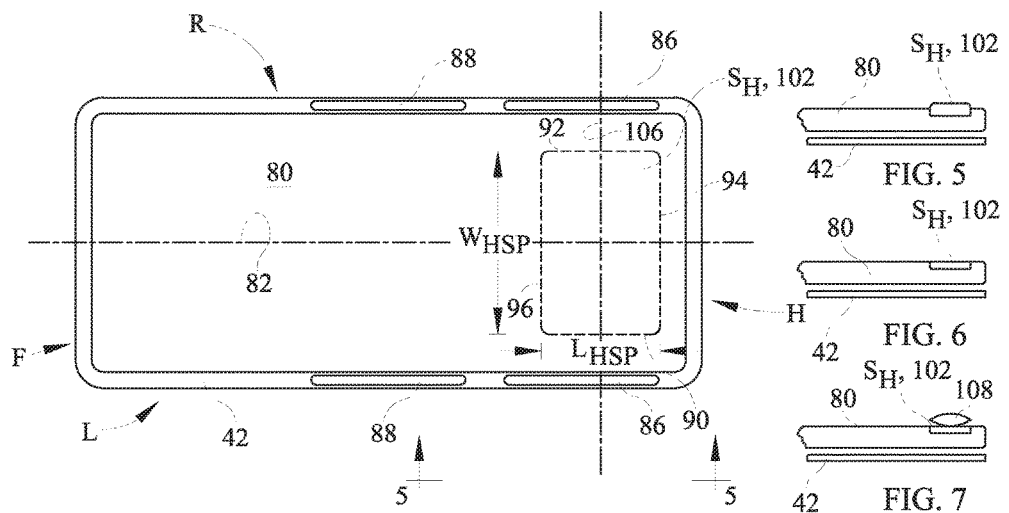
FIG. 4
FIG. 5
FIG. 6
FIG. 7

| 1 | 2 | 3 Sustained | 4 One-Time Transition | 5 Repetitive Transitions |
|---|---|---|---|---|
| | High (e.g. 10 lbs) | [1] Present/Resting | | |
| | Low (e.g. 3 lbs) | [2] Present/Resting? Possibly Offset Laterally | | |
| | Zero (e.g. 0 lbs) | [3] Absent Possible egress | | |
| Reading History | Zero → High (e.g. 0 →10) | | [4] Absent → Present | [10] Placing Head on Pillow/Lifting Head from Pillow Possible agitation or discomfort |
| | High → Zero (e.g. 10 →0) | | [5] Present → Absent | |
| | Zero → Low (e.g. 0 →3) | | [6] Absent → Present, Possibly Offset (reduced confidence) or Lateral movement from in range to out of range. | [11] Placing Head on edge of pillow/Lifting head from edge of pillow Possible lateral offset Possible agitation or discomfort Possible repeated lateral movement from out of range to in range or vice versa |
| | Low → Zero (e.g. 3 →0) | | [7] Present → Absent, Possibly Offset (reduced confidence) or Lateral movement from in range to out of range. | |
| | Low → High (e.g. 3 →10) | | [8] Present, moving toward center | [12] Left to Right or Right to Left Transition. Possible Agitation or discomfort. |
| | High → Low (e.g. 10 →3) | | [9] Present, moving away from center | |

FIG. 18

| | | Lateral Position History | |
|---|---|---|---|
| | | 1 | 2 |
| | | Sustained Lateral Position<br><br>L ———<br>C ———  OR<br>R ——— | Repetitive Lateral Movement (e.g. alternating)<br><br>L ⎤⎡⎤⎡⎤⎡<br>R |
| Vertical History | 1 | Sustained Presence<br><br>P ⎤⎡⎤⎡⎤⎡<br>A | 1 acceptable<br>patient is resting | 4 other than acceptable<br>unacceptable<br>mildly unacceptable<br>problem other than egress |
| | 2 | Repetitive Presence and Absence (e.g. alternating)<br><br>P ⎤⎡⎤⎡⎤⎡<br>A | 2 other than acceptable<br>unacceptable<br>mildly unacceptable<br>problem other than egress | 5 other than acceptable<br>unacceptable<br>moderately unacceptable<br>problem other than egress |
| | 3 | Sustained Absence<br><br>P ⎤———<br>A | 3 other than acceptable<br>unacceptable<br>possible egress | 6 other than acceptable<br>unacceptable<br>possible egress |

FIG. 26

| | | Risk Assessment | | | |
|---|---|---|---|---|---|
| | | 1 | 2 | 3 | 4 |
| | | Patient Position Monitoring System | Head Siderail | Foot Siderail | Elevation |
| | | NOT ARMED | DOWN | DOWN | NOT LOW |
| Sensor History | | | | | |
| Vertical | Sustained Presence | 1 Low | 6 Low | 11 Low | 16 Low |
| | Persistent Presence/Absence | 2 Low-Med | 7 Medium | 12 Med-High | 17 Medium |
| | Sustained Absence | 3 Low-Med | 8 Med-High | 13 High | 18 Med-High |
| Lateral | Sustained Lateral Position | 4 Low | 9 Low | 14 Low | 19 Low |
| | Persistent Lateral Movement | 5 Medium | 10 Med-High | 15 Med-High | 20 Med-High |

FIG. 34

METHOD AND APPARATUS FOR MONITORING AND REPORTING ON THE STATUS OF AN OCCUPANT OF AN OCCUPANT SUPPORT

TECHNICAL FIELD

The subject matter described herein includes a method for monitoring and reporting on the status of an occupant of an occupant support such as a hospital bed. The subject matter described herein also includes an instrumented head support, such as a pillow or a head support portion of a mattress, which is useful in carrying out the method.

BACKGROUND

It is desirable to monitor hospital patients while they are resting in a bed so that if a condition of concern arises the condition can be promptly and accurately reported to a caregiver. Certain conditions of concern include discomfort, restlessness, agitation, and attempts by the patient to attempt an unauthorized egress from the bed.

SUMMARY

A method for monitoring an occupant of an occupant support includes the steps of 1) establishing a lateral position history of the occupant to assess how frequently the occupant's head undergoes a lateral transition on a head support, 2) establishing a vertical position history of the occupant which accounts for how frequently the occupant's head is applied to and removed from the head support, and 3) if the lateral position history indicates repetitive lateral movement or the vertical history indicates other than sustained presence of the occupant's head on the head support, reporting that the occupant is in a state other than an acceptable state. In one embodiment the accounting of how frequently the occupant's head is applied to and removed from the head support is an accounting of how frequently the weight of the occupant's head is applied to and removed from the head support. In other embodiments the accounting may be carried out in other ways, for example by using video surveillance to establish the vertical position of the occupant's head relative to the pillow, including, when the occupant's head is touching the pillow, the extent to which the occupant's head sinks into the pillow.

Another method for monitoring an occupant of an occupant support includes 1) establishing a spatial and temporal relationship of the occupant's head relative to a head support, 2) acquiring information from at least one source other than the head support, and 3) producing an occupant status report which depends on the spatial and temporal relationship and on the information from the other source.

A head support useful for carrying out the methods includes a monitoring package associated with the head support. The monitoring package includes an instrumentation package, a processor and a memory. The instrumentation package includes at least one sensor for sensing a parameter. In one embodiment the parameter is a force related parameter. The processor is adapted to execute instructions for 1) establishing a relationship of a person's head relative to the head support based on information acquired from the sensor or sensors, and 2) producing a report of the person's state based on the relationship.

BRIEF DESCRIPTION OF THE DRAWINGS

The foregoing and other features of the various embodiments of the method and apparatus for monitoring an occupant of an occupant support described herein will become more apparent from the following detailed description and the accompanying drawings in which:

FIG. 2 is a schematic plan view of the bed of FIG. 1 showing an instrumented pillow on the mattress.

FIG. 3 is a partial left side elevation view of the bed of FIG. 1.

FIG. 4 is a schematic plan view similar to that of FIG. 2 but showing a mattress with an instrumented head support portion.

FIGS. 5-7 are partial left side elevation views of the bed of FIG. 4 showing variations of the head support portion and the use of a conventional pillow in combination with an instrumented head support portion.

FIG. 18 is a lookup table for one of the steps of the method of FIG. 17.

FIG. 26 is a lookup table for one of the steps of the method of FIG. 24.

FIG. 34 is a lookup table showing an occupant risk assessment as a function of position history of the occupant's head with respect to a head support and information from a source other than the head support.

DETAILED DESCRIPTION

Figure 1:
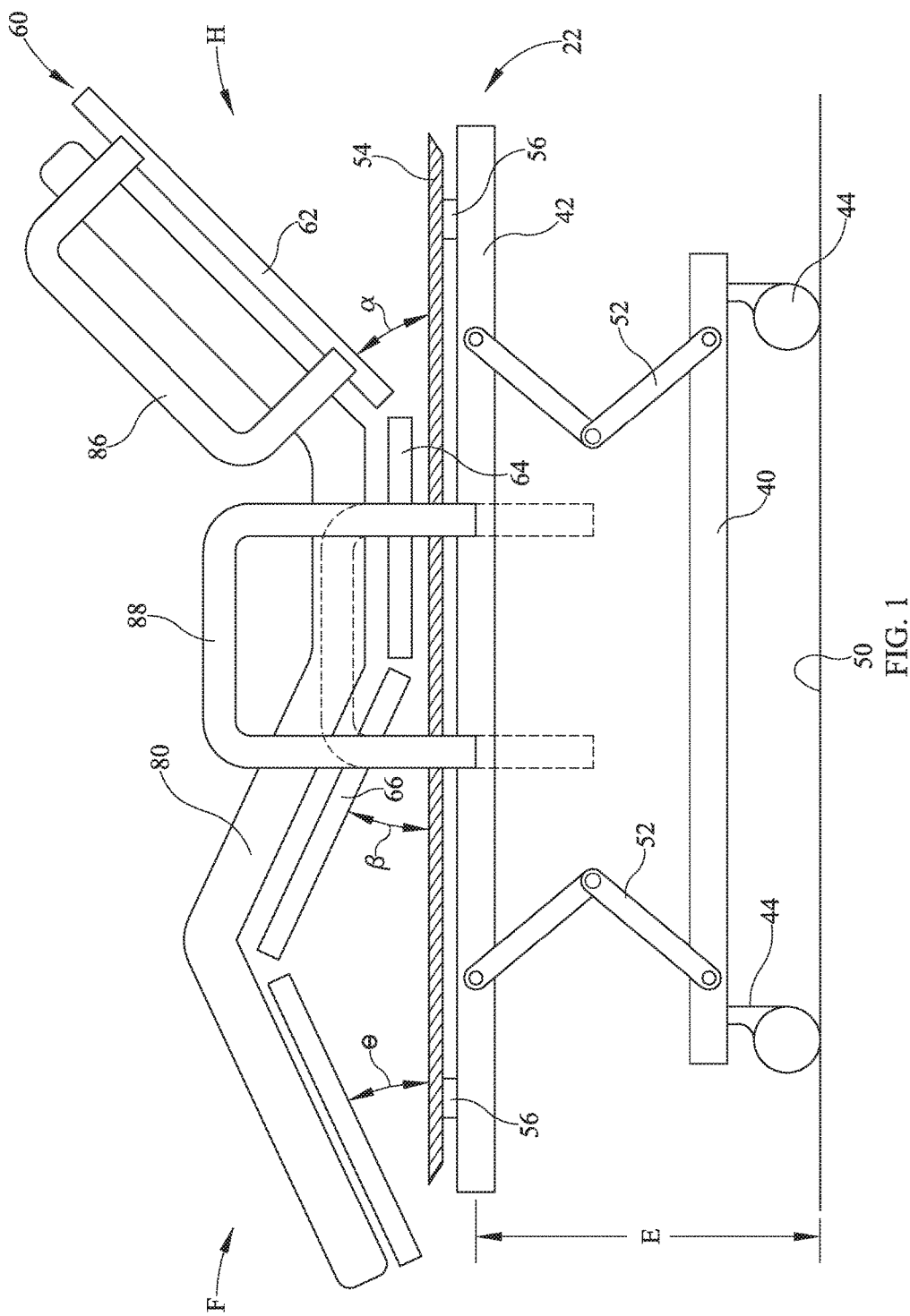
FIG. 1 is a schematic left side elevation view of an occupant support illustrated as a hospital bed including a mattress.

Referring to FIG. 1, an occupant support 38, illustrated as a hospital bed, includes a base frame 40 and an elevatable frame 42. The bed extends longitudinally from a head end H to a foot end F and extends laterally from a left side L, seen in the FIG. 1, to a right side R seen in FIGS. 2 and 4. Casters 44 extend from the base frame to the floor 50. A lift system 52, illustrated as a set of links, connects the base frame to the elevatable frame. The lift system also includes actuators, not illustrated, for raising and lowering the elevatable frame relative to the base frame. A weigh frame 54 is supported on the elevatable frame so that load cells 56 react the combined weight of the weigh frame, the weight of any bed components supported by the weigh frame, and the weight of an occupant occupying the bed. The bed includes four load cells, one on the left side of the bed near the head end, one on the left side near the foot end, and two similarly positioned on the right side of the bed.

The weigh frame supports a segmented deck 60 comprised of an upper body or torso section 62 corresponding approximately to an occupant's torso. The upper body section 62 is orientation adjustable through an angle α from a substantially horizontal orientation (0°) to a more vertical orientation. The deck also includes a seat section 64 corresponding approximately to an occupant's buttocks, a thigh section 66 corresponding approximately to an occupant's thighs, and a calf section 68 corresponding approximately to an occupant's calves. The calf and thigh sections are orientation adjustable through angles θ and β from a substantially horizontal orientation to a less horizontal orientation. Actuators, not illustrated, are provided to adjust the orientation angles α, θ, and β of the upper body, thigh and calf sections so that a user can change the profile of the bed between a flat profile (α=θ=β=0) and a profile in which at least one of α, θ, and β is nonzero.

The bed also includes a mattress 80 resting atop the deck. The mattress is flexible enough to conform to the profile of the deck. The mattress has a longitudinally extending centerline 82.

The bed also includes head and foot siderails 86, 88 on both the left and right sides of the bed. The head siderails are secured to deck torso section 62 so that the orientation of each head siderail changes along with the orientation angle of the torso section. The foot siderails are attached to the elevatable frame 42. The head and foot siderails are movable between a deployed position, illustrated with solid lines, and a stowed position illustrated with dashed lines for the foot siderail only.

The bed may also include an occupant position monitoring system, also known as a patient position monitoring system or PPM system. An example PPM system is described in U.S. Pat. No. 6,208,250, the contents of which are incorporated herein by reference. The system disclosed in U.S. Pat. No. 6,208,250 has three levels of sensitivity which can be selected by a user, usually a caregiver. When the PPM system is armed, it activates an alarm if the position of the patient violates position criteria associated with the selected sensitivity level. The lowest sensitivity setting results in activation of the alarm only if the occupant actually exits the bed. A moderate sensitivity setting results in activation of the alarm if the occupant assumes a position on the bed consistent with an intent to exit. The most sensitive sensitivity setting results in activation of the alarm if the occupant merely moves away from a defined position on the bed, for example if the occupant migrates laterally away from the center of the bed and toward the left or right edge of the bed by more than an acceptable amount, or if the occupant sits up from a lying position. If the occupant is under no restrictions as to his or her movement, including being cleared to exit the bed without assistance or supervision, the caregiver may disarm the system, in which case the alarm remains inactive irrespective of occupant position.

Figure 8:
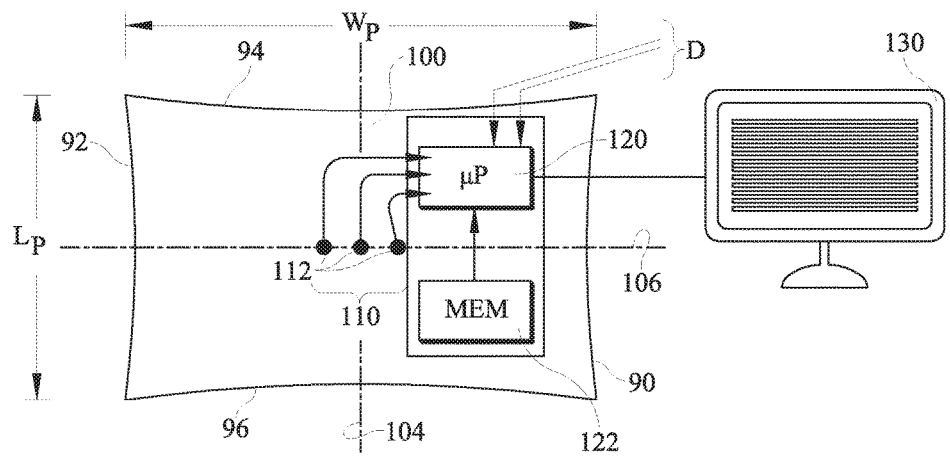
FIGS. 8-10 are plan views of an instrumented pillow, such as the pillow of FIG. 2, showing various arrangements of processor and memory components.

Referring additionally to FIGS. 3 and 5-7, the bed includes an instrumented head support $S_H$ upon which the bed occupant may rest her head. One example of an instrumented head support is a pillow 100 shown in FIGS. 2-3. The pillow is a stand alone component rather than a component of the bed or mattress 80. The pillow has a length $L_P$ (which may also be referred to as a lengthwise dimension or a longitudinal dimension) and a width $W_P$ (which may also be referred to as a widthwise dimension or a lateral dimension). As with a conventional sleeping pillow, width $W_P$ is larger than length $L_P$. The pillow is typically oriented on the mattress with its lengthwise dimension $L_P$ parallel to mattress longitudinal centerline 82 and its widthwise dimension $W_P$ perpendicular to centerline 82. The pillow has a left edge 90, a right edge 92, a headward edge 94, and a footward edge 96. The pillow includes a longitudinally extending pillow centerline 104 (seen best in FIG. 8) midway between the left and right edges, and a laterally extending pillow centerline 106 midway between the head and foot edges. In FIG. 8 and subsequent illustrations the left edge of the pillow is at the right side of the illustration, and the right edge of the pillow is at the left side of the illustration. This is because the pillow is shown as if the headward and footward edges of the bed were at the top and bottom respectively of the illustration, with left and right being defined from the perspective of an occupant lying face up on the mattress.

Another example of an instrumented head support $S_H$ is a head support portion 102 of mattress 80 as seen in FIGS. 4-7. Analogous features of the head support portion 102 and pillow 100 are identified by the same or similar reference numerals. The head support portion may be raised above the upper surface of the mattress as seen in FIG. 5 or may be substantially flush with the upper surface of the mattress as seen in FIG. 6. As seen in FIG. 7, if the head support portion is flush, a conventional pillow 108 may be provided to improve occupant comfort. The conventional pillow, if provided, is placed over the instrumented head support portion. The instrumented head support portion 102 of the mattress, like pillow 100 described above, has a length $L_{HSP}$ (which also be referred to as a lengthwise dimension or a longitudinal dimension) and a width $W_{HSP}$ (which may also be referred to as a widthwise dimension or a lateral dimension). As with a conventional sleeping pillow, width $W_{HSP}$ is larger than length $L_{HSP}$. The head support portion is typically arranged so that its lengthwise dimension $L_{HSP}$ is parallel to mattress longitudinal centerline 82 and its widthwise dimension $W_{HSP}$ is perpendicular to centerline 82. The head support portion has a left edge 90, a right edge 92, a headward edge 94, and a footward edge 96. Left and right are taken from the perspective of an occupant lying face up on the mattress. The head support portion also includes a longitudinally extending head support portion centerline 104 (analogous to pillow longitudinal centerline 104) midway between the left and right edges, and a laterally extending head support portion centerline 106 (analogous to pillow lateral centerline 106) midway between the head and foot edges.

Irrespective of whether the head support is a pillow or a portion of the mattress, the head support includes an on-board monitoring package. The monitoring package is referred to as "on-board" because all of its components are sub-elements of the pillow or of the head support portion of the mattress as the case may be. Referring to FIG. 8, the on-board monitoring package includes, at a minimum, an instrumentation package such as a sensor array 110 comprised of at least one sensor 112. In one embodiment the sensor senses a force related parameter. As used herein a force related parameter includes both force and pressure (force per unit area). Accordingly the sensor is a force sensor such as a load cell or a pressure sensor.

Figure 9:
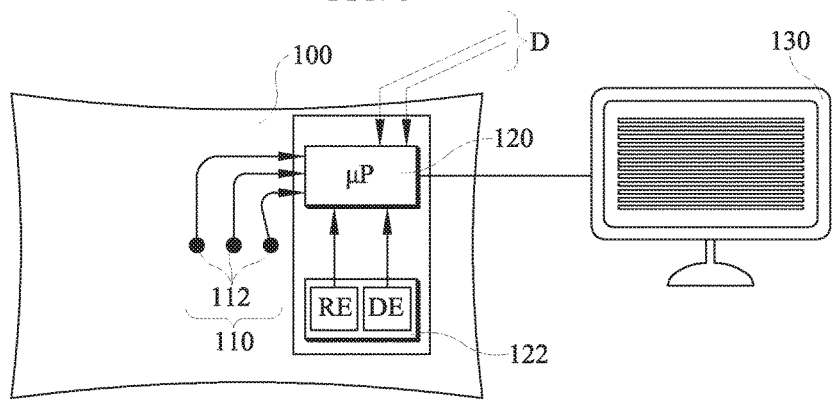
Figure 10:
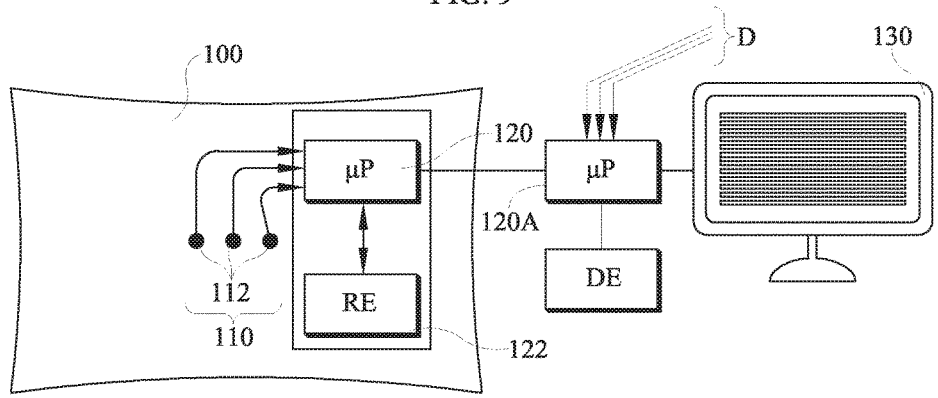

The on-board monitoring package may also include a processor such as microprocessor 120 which receives signals from the sensor, and a memory 122 whose contents include, among other things, instructions which are executable by the processor. As seen in FIG. 9 the instructions and/or the portions of the memory in which the instructions are stored may be physically or notionally separated into a rules engine RE and a decision engine DE. The instructions of the rules engine are instructions that process data from the instrumentation package. The instructions of the decision engine are instructions that also process data from the instrumentation package (which data may have been preprocessed by processor 120) but, as part of the processing, also account for data from sources other than the instrumentation package. Such data from other sources may include data from a PPM system and data from sensors indicating siderail position (stowed or deployed) and are indicated by arrows D leading into the processor. In another alternative seen in FIG. 10, the rules engine may be a component of the on-board package while the decision engine and an associated second processor 120A are off-board. Off-board components are those which are not sub-elements of the pillow or head support portion of the mattress. Off-board components may nevertheless be components of the bed or may be elements located at an off-bed location. The foregoing is not intended to be a comprehensive description of all possible architectures and distributions of the instrumentation package, processor, and memory. Irrespective of the architecture used, the output of processor 120 or 120A is communicated or reported to a display, exemplified as a video monitor 130.

As described in more detail below, the sensor or sensors of the instrumentation package are provided to monitor the spatial and temporal relationship of the occupant's head relative to the pillow. Among these relationships are whether or not the occupant's head is resting on the pillow, where the occupant's head is positioned relative to one or more datums such as centerlines 104, 106 or edges 90, 92, 94, 96, and the history of any changes in the position of the occupant's head.

FIGS. 11-16 show several variations of an instrumentation package useful for the apparatus and method described herein. Each instrumentation package of FIGS. 11-16 includes a sensor array 110 comprised of at least one sensor 112. The sensor or sensors may be a sensor or sensors for sensing a force related parameter. In each variation the head support is illustrated in the form of a pillow 100 rather than a head support portion 102 of mattress 80, however the principles disclosed herein are applicable to both kinds of head support.

Figure 11:
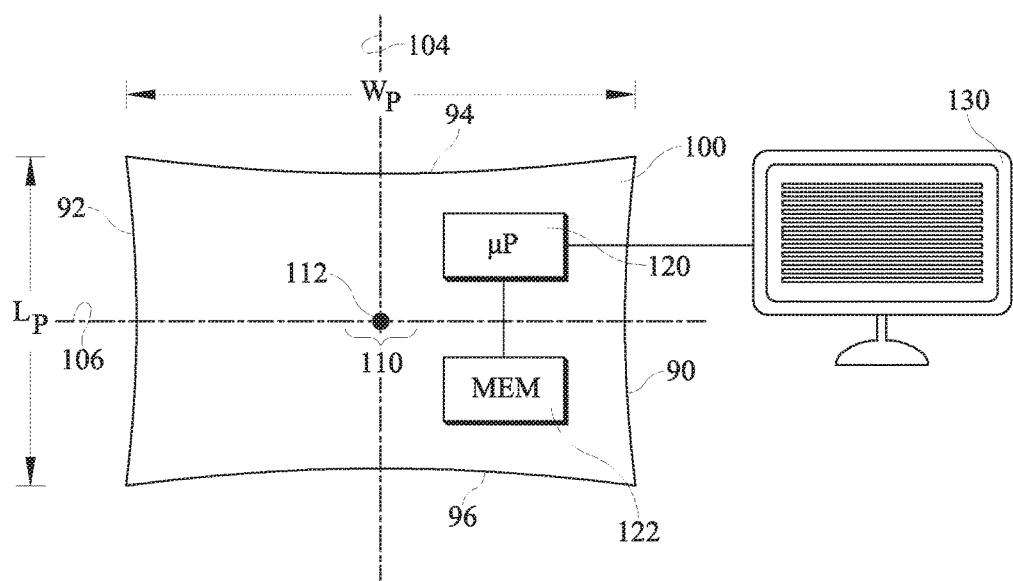
FIGS. 11-16 are plan views of the instrumented pillow of FIGS. 8-10 showing various layouts of an instrumentation package which comprises one or more sensors and which is useful for the apparatus and method described herein.

The instrumentation package of the pillow of FIG. 11 comprises a sensor array having only one sensor 112. In the illustration sensor 112 is positioned at the intersection of pillow longitudinal and lateral centerlines 104, 106. In practice it is believed that the sensor should be laterally positioned at the longitudinal centerline 104 (i.e. laterally midway between left and right edges 90, 92) but that longitudinal positions other than at the lateral centerline 106 may be satisfactory or even desirable.

Figure 12:
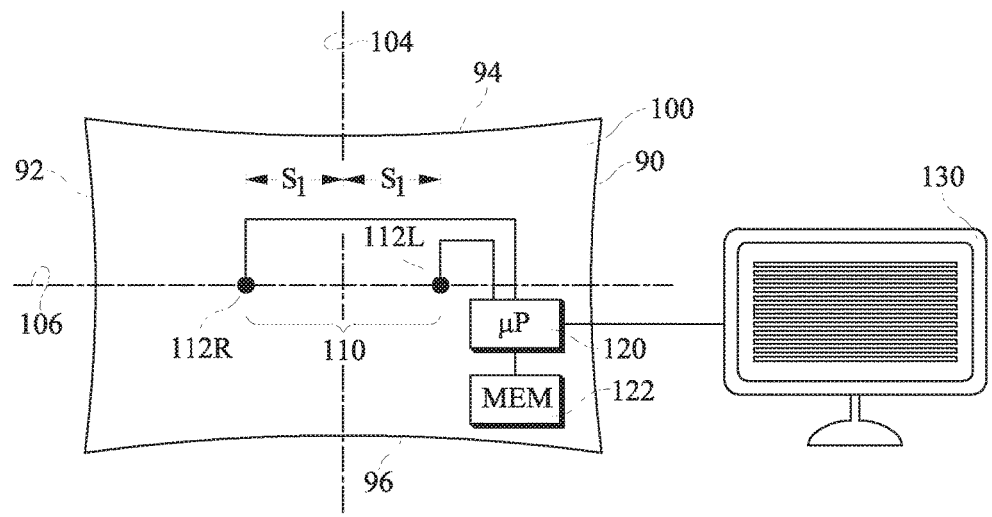
Figure 13:
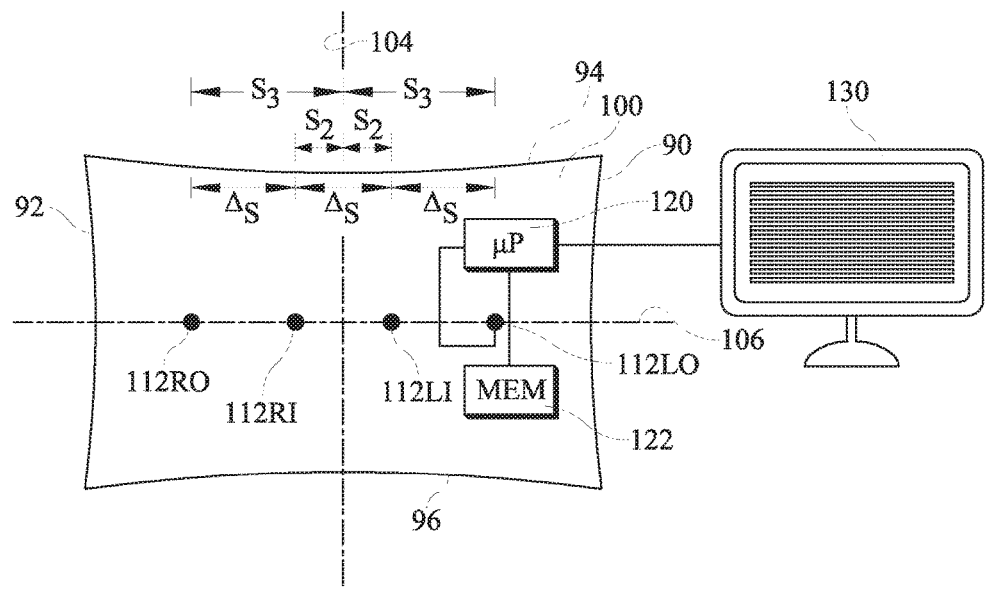
Figure 14:
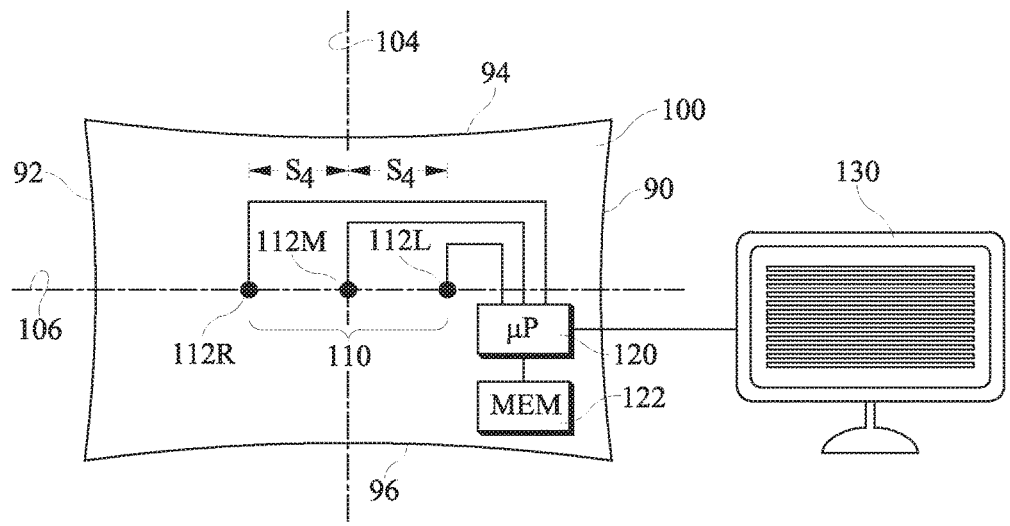
Figure 15:
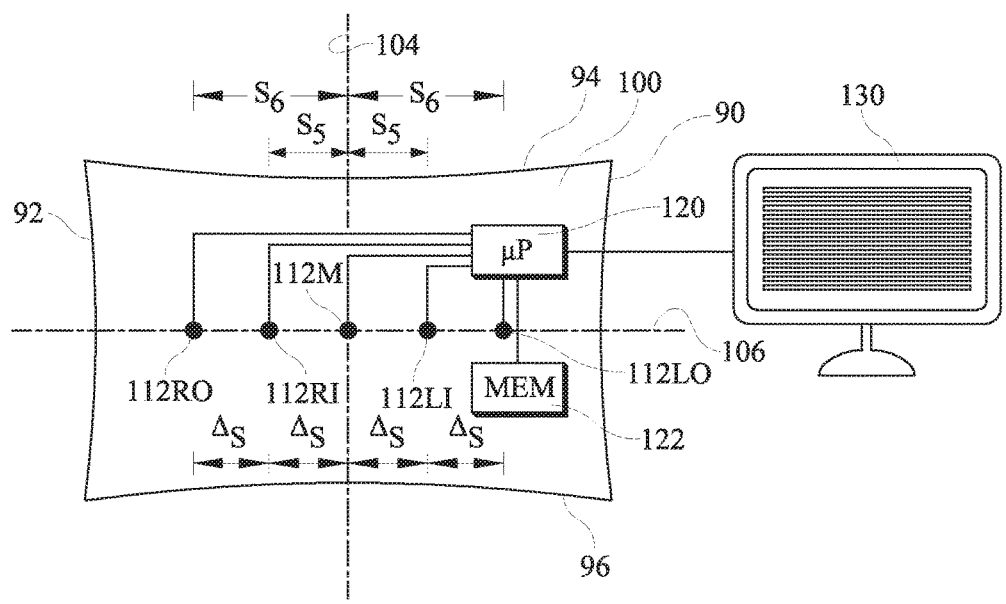

The instrumentation packages of FIGS. 12-15 each comprise a sensor array 110 having multiple sensors 112 arranged in a single, substantially laterally extending row. FIGS. 12 and 13 illustrate sensor arrays having an even number of sensors. In FIG. 12 left and right sensors 112L, 112R are equally spaced from longitudinal centerline 104 by spacing S1. In FIG. 13, left and right inboard sensors 112LI, 112RI are equally spaced from centerline 104 by spacing S2, and left and right outboard sensors 112LO, 112RO are equally spaced from centerline 104 by spacing S3. The intersensor spacing ΔS may or may not be equal and need not be the same for all pairs of sensors. FIGS. 14 and 15 illustrate sensor arrays having an odd number of sensors. In both cases one sensor, 112M, is a middle sensor positioned at longitudinal centerline 104. In FIG. 14 left and right sensors 112L, 112R are equally spaced from longitudinal centerline 104 (and therefore from middle sensor 112M) by spacing S4. In FIG. 15, left and right inboard sensors 112LO, 112RI are equally spaced from centerline 104 by spacing S5, and left and right outboard sensors 112LO, 112RO are equally spaced from centerline 104 by spacing S6. The intersensor spacing ΔS may or may not be equal and need not be the same for all pairs of sensors.

Figure 16:
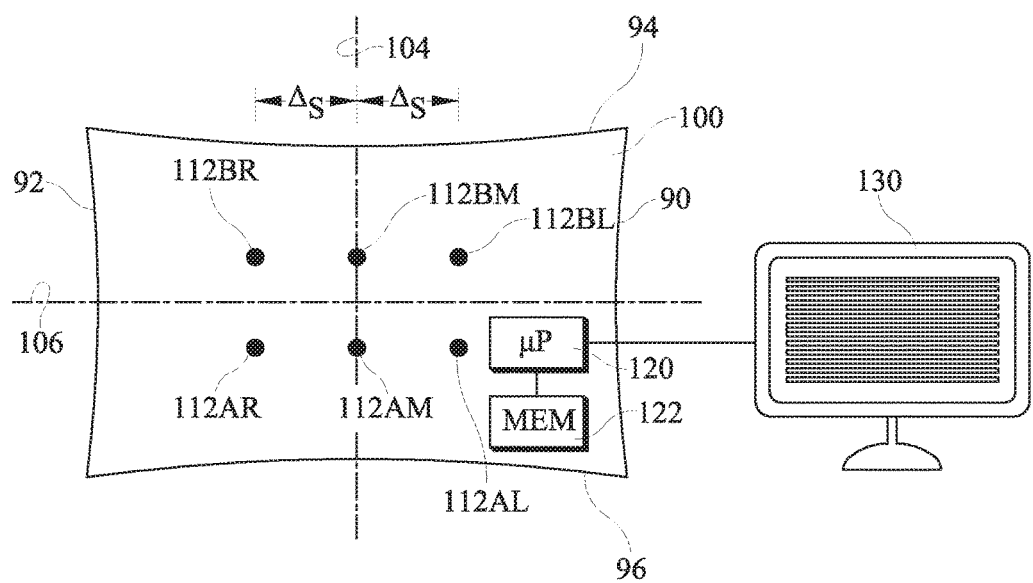

The instrumentation package of FIG. 16 comprises a sensor array having multiple sensors arranged in multiple, substantially laterally extending rows indicated by letter A or B after numeral 112. Each row may have an even or odd number of sensors laterally distributed as described above in connection with the single row embodiments. As illustrated the sensors are arranged in a two row by three column array with an equal quantity of sensors in each row and an equal quantity of sensors in each column. However unequal quantities may also be used. Moreover the sensors in any given row may be laterally offset or staggered from the sensors in another row. To the extent the location of the occupant's head, and changes thereto, in the lateral direction are considered to be more important than the location of the occupant's head, and changes thereto, in the longitudinal direction, it is believed that the number of columns should exceed the number of rows because it is believed that the data obtained from laterally distributed sensors will be more meaningful than the data obtained from longitudinally distributed sensors. Moreover, it is believed that the information obtained from an odd quantity of sensors in a row, with one sensor centered between left and right pillow edges 90, 92, is more advantageous than information obtained from an even quantity of sensors because the former arrangement can provide a higher confidence indication of whether or not the occupant's head is laterally centered on the pillow.

Figure 17:
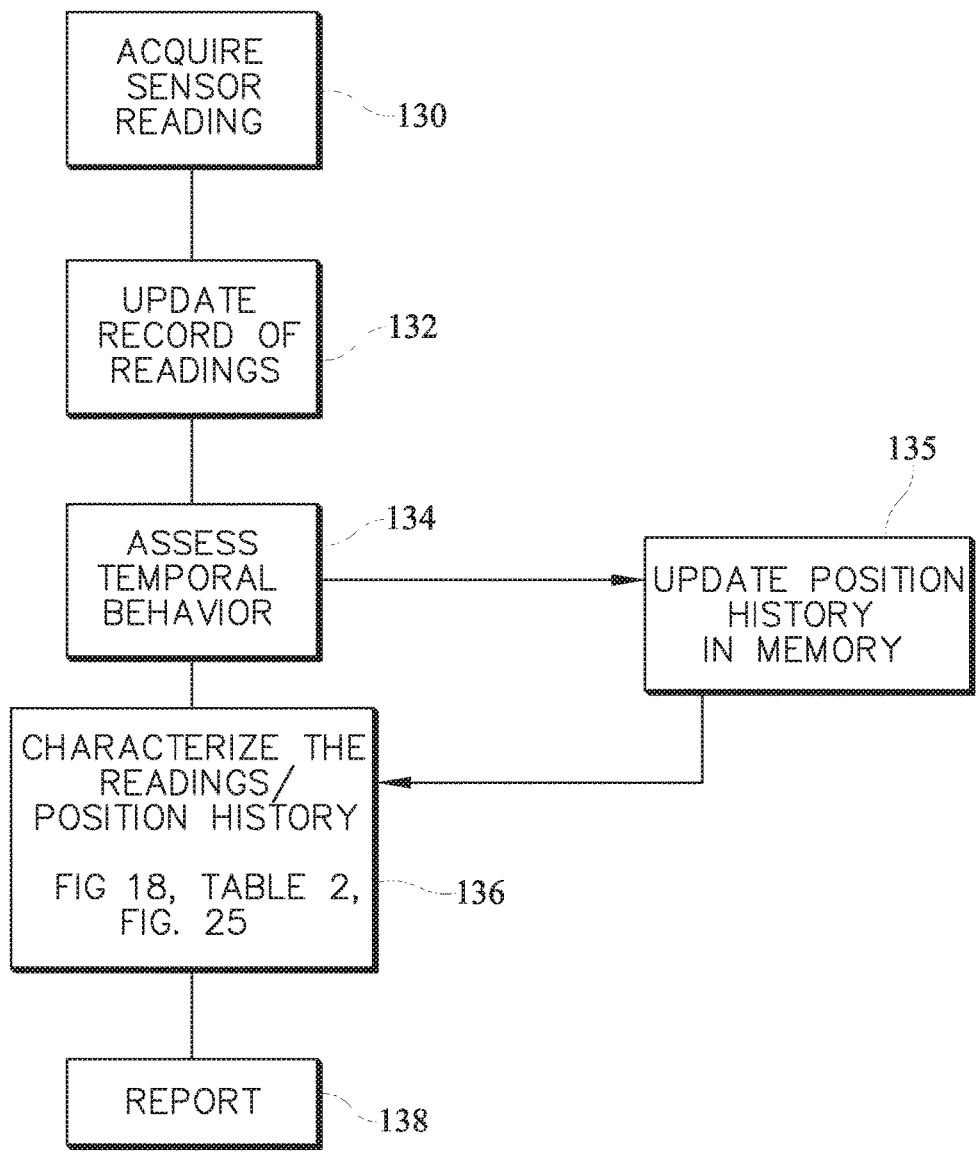
FIG. 17 is a block diagram of a first method for monitoring an occupant of the occupant support in which the instrumented pillow or other head support includes only a single sensor.

FIGS. 17-18 disclose a first method for monitoring an occupant of the occupant support. The method of FIGS. 17-18 employs the pillow embodiment of FIG. 11, i.e. the embodiment in which the instrumentation package includes only a single sensor 112 for sensing a parameter, for example a force related parameter. According to the method, processor 120 receives readings from the sensor at successive points in time and executes instructions from memory 122 to determine the state of the occupant. At block 130 the method acquires a current sensor reading. At block 132 the method updates a temporal record of readings in memory 122 by adding the acquired reading to the record. The method may also select a set of relevant readings to use in one or more subsequent steps. In one example the set of relevant readings includes all the readings no older than t time units. In another example the set of relevant readings includes the current reading and one or more previous readings without regard for the age of the readings.

The method then proceeds to block 134 where it assesses the temporal attributes of the record of relevant readings. The assessment step enables the method to distinguish among a sustained reading, a one-time transient, and a repetitive transient. Criteria for distinguishing among these types of events are described later in this specification in connection with FIGS. 19-23. As shown at block 135 the assessment step also enables the method to develop a historical record of the position of the occupant's head, which record is stored in memory 122 for later use.

The method then proceeds to block 136 where it characterizes the readings from the sensor. Specifically, the method characterizes the position history of the occupant's head which has been developed from the readings from the sensor. The method as illustrated uses a lookup table stored in memory 122 to carry out the characterization. An example of such a table is the table of FIG. 18, selected cells of which are numbered for ease of reference in the following discussion. Column 2 of the table shows possible sensor reading histories (e.g. high, low, zero, zero to high, low to zero). In the illustrated embodiment the high, low and zero readings are represented by weight (or pressure) within a tolerance. The weight of a typical adult human head is about 10 pounds (approximately 4.5 kilograms). Therefore a high reading may be a reading on the order of about 10 pounds, for example 9.5 to 10.5 pounds. A high reading of about 10 pounds from sensor 112 indicates that the occupant's head is present on the pillow, and approximately coincides with the location of the sensor (centered on the pillow in the example of FIG. 11). A reading of approximately zero indicates that the occupant's head is absent from the pillow. Alternatively a reading of approximately zero may indicate that the occupant's head is resting on the pillow but is too remote from the sensor (e.g. near an edge 90, 92, 96) to transfer any significant weight to the sensor. (This condition may be referred to as being beyond the range of the sensor.) A low reading (for example 3 pounds) may be an indicator that the occupant's head is present, but is offset from the location of the sensor to a location in which the pillow transfers some, but not all, of the weight of the occupant's head to the sensor. Therefore the low reading may indicate that the occupant's head is laterally offset to the left or right of the sensor or longitudinally footwardly of the sensor, but not so far as to cause the sensor to produce a reading of zero or approximately zero. Other readings may also be accounted for. For example a moderate reading such as 5 pounds may indicate that the occupant's head is near the headward edge 94 of the pillow, such that her neck overlies the sensor and therefore causes more weight transferal to the sensor than would be the case if her head were offset toward the footward, left or right edges, but less weight transferal than if her head were immediately over the sensor. In the interest of explanatory simplicity the following discussion does not account for longitudinal offsets and "moderate" readings as just described, but instead considers only the high, low and zero readings, and treats a low reading as corresponding to a lateral offset of the occupant's head but still within the range of the sensor.

If the sensor reading is a sustained high reading, the method reports that the occupant's head is present on the pillow and/or that the occupant is resting (cell 1). If the sensor reading is a sustained low reading, the method reports that the occupant's head is or may be present on the pillow but, if present, is offset from the location of the sensor to the left or right (cell 2). If the sensor reading is a sustained reading of approximately zero, the method reports that the occupant's head is absent from the pillow (cell 3). This may also be an indication that the occupant is engaged in some action which may be of concern (e.g. an unauthorized attempt to exit from the bed) or may not be of concern (e.g. the occupant is sitting up to drink water).

If the sensor reading is not a sustained reading the method may report a transient event. For example if the sensor reading shows a "one-time" transition from a reading of approximately zero to a high reading, the method reports a transition from the occupant's head being absent to the occupant's head being present (cell 4). If the sensor reading shows a one-time transition from a high reading to a reading of approximately zero, the method reports a transition from the occupant's head being present to the occupant's head being absent (cell 5). If the sensor shows a one-time transition from zero to low or low to zero, the method reports a transition from absent to present or present to absent (cells 6 and 7 respectively) but with a lower confidence than in the case of the zero/high and high/zero transitions and/or with an indication that the occupant's head is (or had been) laterally offset from the pillow. A one-time zero to low transition may also indicate that the occupant has moved her head laterally on the pillow from a location out of range of the sensor to a location in range of the sensor but not immediately over the sensor, while a one time low to zero transition may indicate that the occupant has moved her head laterally on the pillow from a location in range of the sensor but not immediately over the sensor to a location out of range of the sensor. If the sensor reading shows a one-time transition from low to high or high to low the method reports that the occupant's head has moved laterally on the pillow either toward the longitudinal centerline (cell 8) or away from the longitudinal centerline (cell 9). The lateral repositionings described above may be a translation of the occupant's head (the occupant has slid her head one way or the other) or a rotation of the occupant's head (the occupant has rocked her head one way or the other). If the low/high or high/low transition includes an interval of time during which the sensor reading is zero, this may indicate that the occupant lifted her head off the pillow as part of the act of repositioning her head laterally.

If the sensor readings show repetitive transitions back and forth from zero to high and high to zero, the method reports that the occupant is repeatedly lifting her head off the pillow and placing it back on the pillow and/or reports that the occupant may be in a state of agitation or discomfort (cell 10) If the sensor readings shows repetitive transitions back and forth from zero to low and low to zero, the method reports that the occupant is repeatedly lifting her head off the pillow and placing it back on the pillow but that the occupant's head is probably offset from the longitudinal centerline 104, and may also report that the occupant is in a state of agitation or discomfort (cell 11). If the sensor readings show repetitive transitions back and forth from low to high and high to low, the method reports that the occupant is repeatedly translating her head laterally or rocking laterally back and forth (cell 12). If the low/high and high/low transition includes an interval of time during which the sensor reading is zero, this may indicate that the occupant lifted her head off the pillow as part of the act of repositioning her head laterally. Either way the low/high and high/low transitions may indicate a state of agitation or discomfort.

At block 138 the processor issues a signal to report the occupant's state. In the example the signal causes video monitor 130 (FIG. 11) to report the state of the occupant. "Report" can refer to the signal emanating from the processor or the information displayed on the monitor despite that fact that intermediate processing may have occurred. Intermediate processing may include actions such as converting digital signals to analogue signals or vice versa and converting electrical signals to video signals or audible signals.

The information contained in a report can be information that merely reports some change (or lack of change) in the state of the spatial and/or temporal relationship of the occupant's head relative to the pillow. However as seen in the foregoing examples the report can involve interpretations such as the interpretation that a pattern of movement suggests that the occupant is agitated or uncomfortable or that the occupant may be intent on exiting the bed. Other interpretations are not precluded. For example a pattern of sensor readings which might be interpreted as agitation or discomfort may instead simply reflect that the occupant is having difficulty falling asleep or is anxious about something. These and other interpretations which are inferable from the sensor data may be reported.

Figure 19:
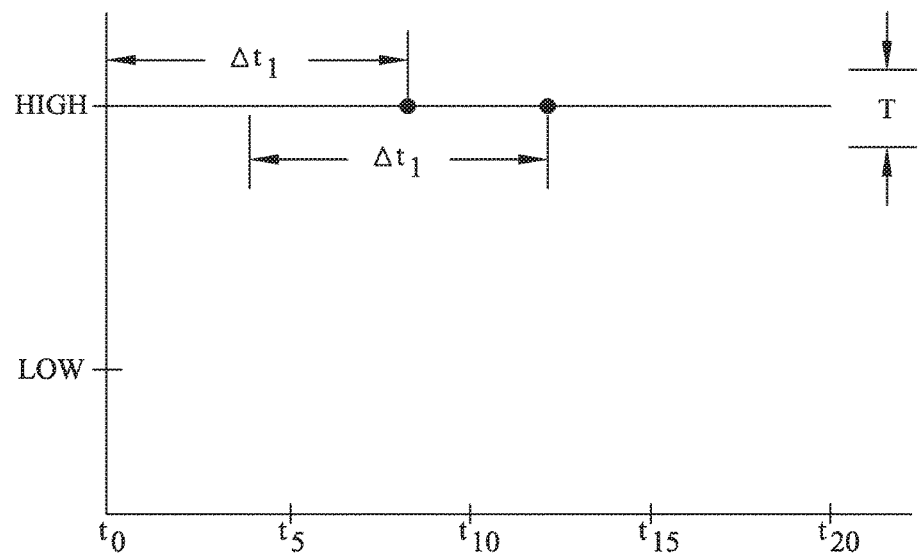
FIGS. 19-23 are a set of graphs illustrating a sustained reading from a sensor, a one-time transient and a repetitive transient.
Figure 20:
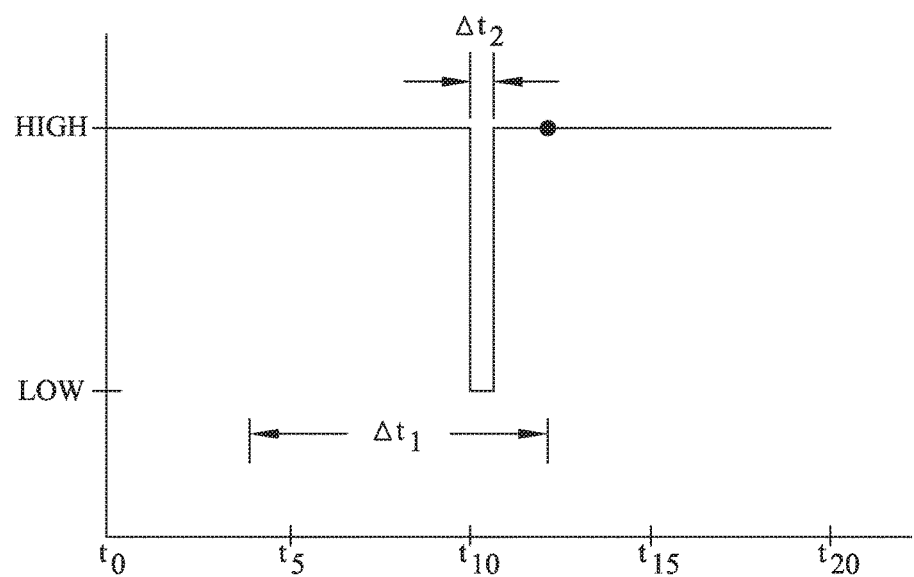
Figure 21:
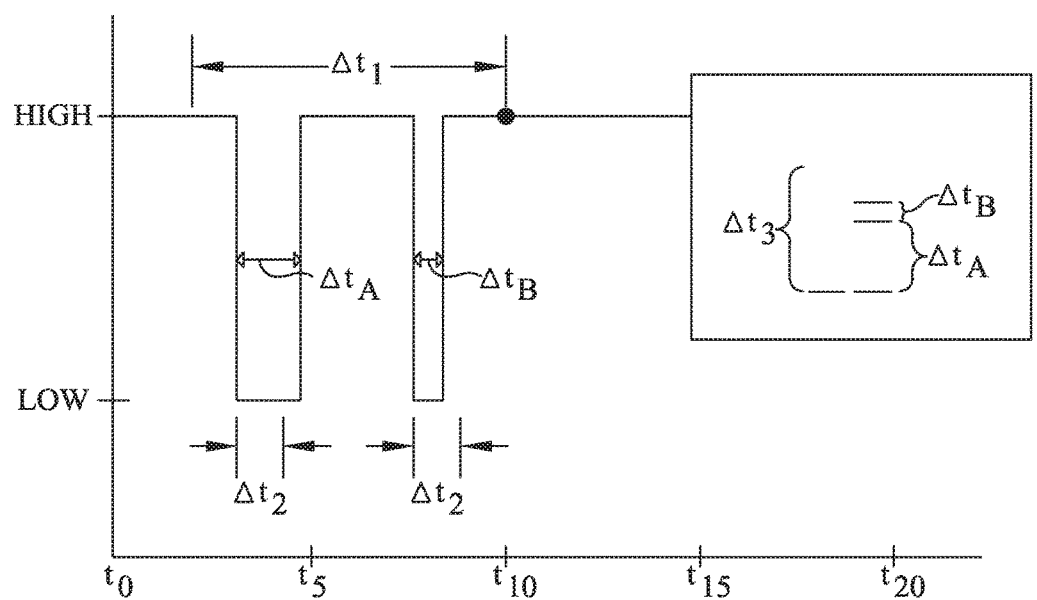

The rules engine includes instructions so that the method can distinguish among the sustained readings, "one-time" transitions, and persistent or repetitive transitions that have been described above in connection with FIGS. 17-18. Referring to FIG. 19, a sustained reading may be one that the instructions of the rules engine recognize as having remained substantially constant (i.e. constant within some tolerance T) for at a prescribed number of time units, for example for least the previous $\Delta t1$ time units. In the example of FIG. 19 the sensor reading at time t8 qualifies as a sustained reading because there has been no deviation from "high" during the previous $\Delta t1$ time units. Similarly, the reading at time t12 also qualifies as a sustained reading. The rules may nevertheless allow for brief anomalies without violating the "substantially constant" criterion. This is seen in FIG. 20 where the rule for declaring that a reading is a sustained reading may be that the reading is constant for at least the previous $\Delta t1$ time units subject to one or more exceptions. One example exception is to disregard bi-directional transitions that take no more than $\Delta t2$ time units. Thus, the reading at time t12 of FIG. 20 qualifies as a sustained reading because even though a bidirectional transition occurred during the preceding $\Delta t1$ time units, its duration was less than $\Delta t2$. Another example is to disregard bi-directional transitions that, taken collectively, add up to no more than $\Delta t3$ time units. This is seen in FIG. 21 where, in the $\Delta t1$ time units prior to t10, two bi-directional transitions occurred, the first of which would have violated the duration criterion of the example of FIG. 20 because its duration, $\Delta tA$, exceeds $\Delta t2$. However because the accumulated duration of both transitions ($\Delta tA+\Delta tB$) is less than $\Delta t3$ time units as seen in the inset at the right of the graph, the sensor reading at t10 is designated a sustained reading. Yet another example is to disregard bi-directional transitions that, taken collectively, add up to no more than $\Delta t3$ time units provided that no individual transition takes more than $\Delta t2$ time units. Under this rule the reading at t10 of FIG. 21 fails the test of a sustained reading because the transition that begins at t3 takes more than $\Delta t2$ time units.

Figure 22:
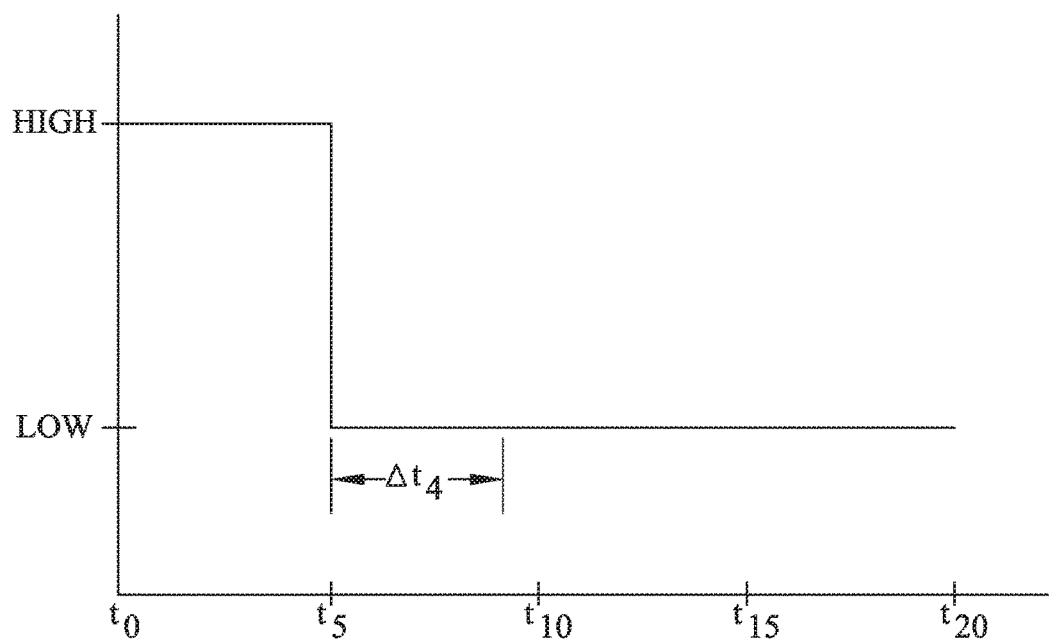

Referring to FIG. 22 a one-time transition may be defined as a reading that transitions from one value (a first value) to another (a second value), and which is unaccompanied by a transition in the opposite direction in a specified number of time units, e.g. $\Delta t4$ time units, following the transition in question.

Figure 23:
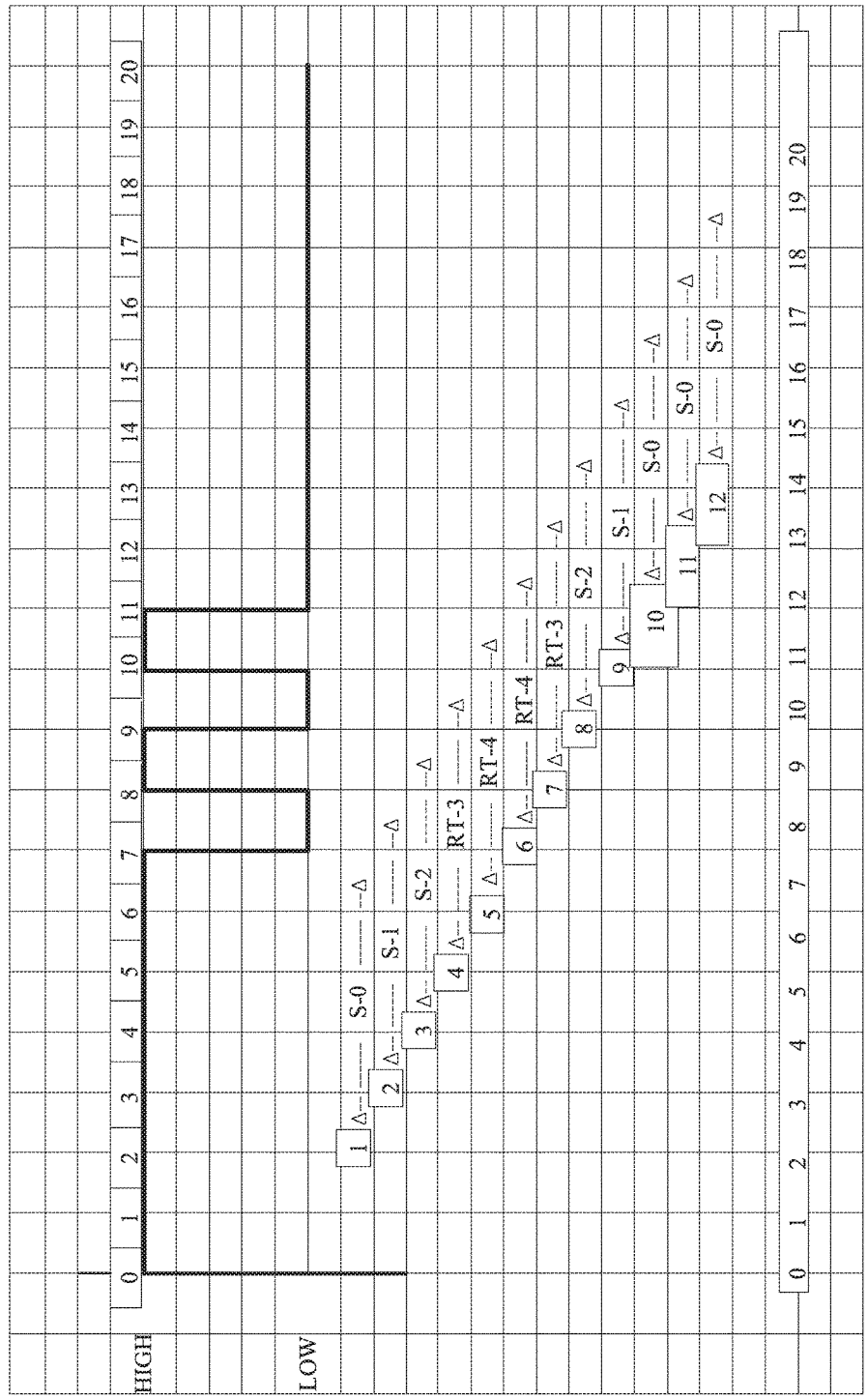

Referring to FIG. 23, a condition of repetitive transitions may correspond to and be detected by a series of readings in which the instructions of the rules engine recognize that at least a specified number of oppositely directed transitions NT have occurred within a time window of no more than a designated number of time units, e.g. $\Delta t5$ time units. In the example of FIG. 23 the specified number of transitions is three (NT=3), and the time window is a sliding time window which is four time units wide ($\Delta t5$=4). In other words the instructions specify that a condition of repetitive transition exists if at least three transitions occur within an interval of no more than four time units. The start and end times of the sliding window are shown by triangles. The window is shown at twelve successive times labeled 1 through 12 just to the left of the start triangle. For example when the window is labelled "2", it brackets times t4 through t7 and represents the temporal reach of the window backward in time at t7; when the window is labelled "8", it brackets times t10 through t13 and represents the temporal reach of the window backward in time at t13. The characters between the start and end triangles shows whether the successive sensor readings within the window are considered to be sustained (S) or are considered to indicate a repetitive transition (RT). The numeral after the hyphen shows the number of transitions occurring within the time window. For example the window labelled "3" encompasses only two transitions, the high to low transition at t7 and the low to high transition at t8. The example rule specifies that this represents a sustained sensor reading, hence the "S-2" between the start and end triangles indicating a sustained condition due to the presence of fewer than three transitions during the time interval. The window labelled "7" encompasses three transitions, the high to low transition at t9, the low to high transition at t10 and the high to low transition at t11. The example rule specifies that this represents a condition of repetitive transition, hence the "RT-3" between the start and end triangles indicating the condition of repetitive transition resulting from three transitions within the sliding window. The content of FIG. 23 is summarized in Table 1 below where S indicates a sustained sensor readings and RT indicates sensor readings in a state of repetitive transition:

TABLE 1

| Window Label | Start time | End time | Transitions in the Window | | | | | Transition count within the Window | Result |
| --- | --- | --- | --- | --- | --- | --- | --- | --- | --- |
| | | | H to L at t7 | L to H at t8 | H to L at t9 | L to H at t10 | H to L at t11 | | |
| 1 | t3 | t6 | No | No | No | No | No | 0 | S |
| 2 | t4 | t7 | Yes | No | No | No | No | 1 | S |
| 3 | t5 | t8 | Yes | Yes | No | No | No | 2 | S |
| 4 | t6 | t9 | Yes | Yes | Yes | No | No | 3 | RT |
| 5 | t7 | t10 | Yes | Yes | Yes | Yes | No | 4 | RT |
| 6 | t8 | t11 | No | Yes | Yes | Yes | Yes | 4 | RT |
| 7 | t9 | t12 | No | No | Yes | Yes | Yes | 3 | RT |
| 8 | t10 | t13 | No | No | No | Yes | Yes | 2 | S |
| 9 | t11 | t14 | No | No | No | No | Yes | 1 | S |
| 10 | t12 | t15 | No | No | No | No | No | 0 | S |
| 11 | t13 | t16 | No | No | No | No | No | 0 | S |
| 12 | t14 | t17 | No | No | No | No | No | 0 | S |

The foregoing examples of distinguishing among sustained readings, "one-time" transitions, and repetitive transitions have been presented in the context of low to high and high to low transitions, however the same principles apply to zero to high, high to zero, zero to low, and low to zero transitions.

Figure 24:
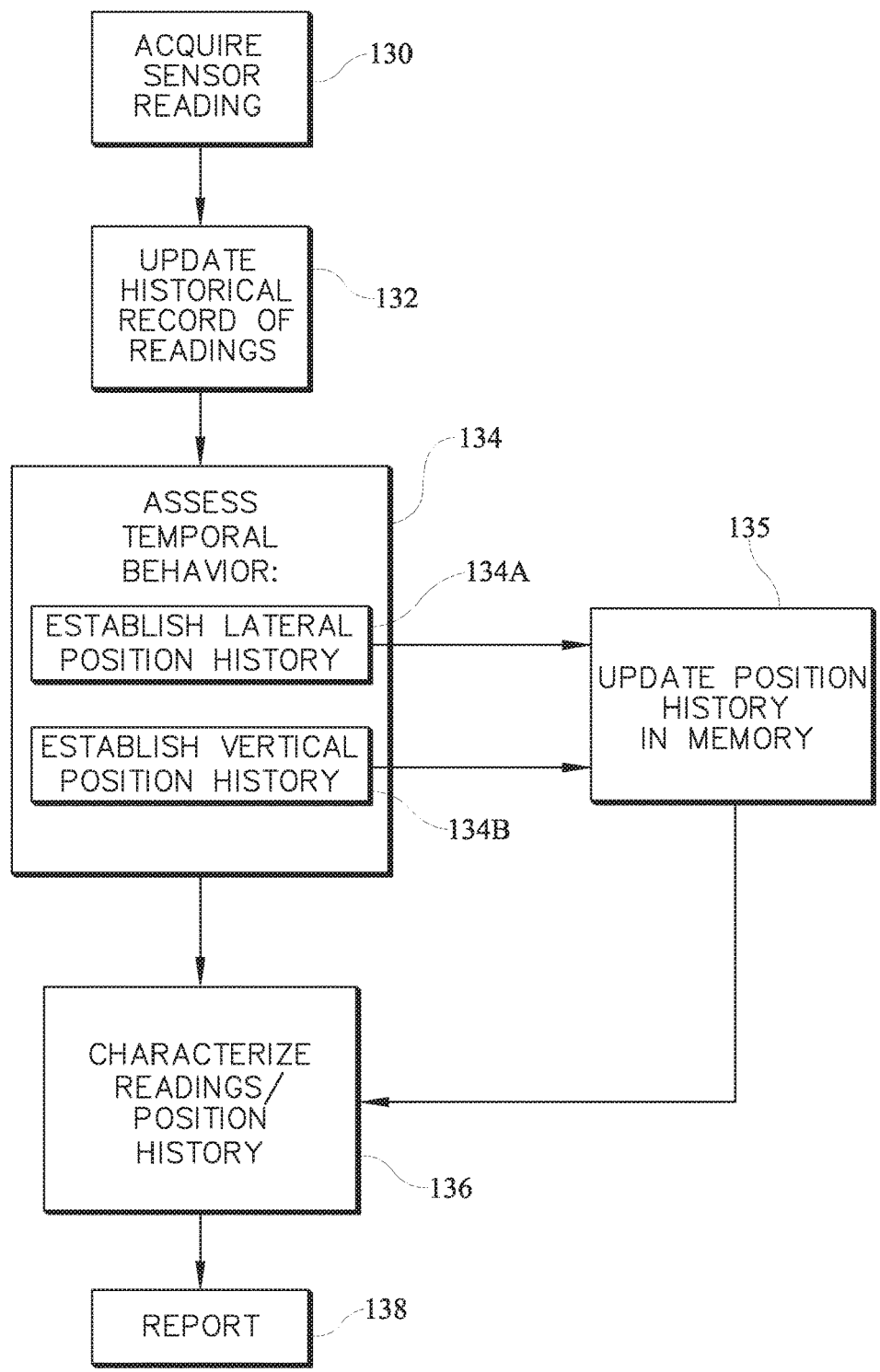
FIG. 24 is a block diagram of a related method for monitoring an occupant of the occupant support in which the instrumented pillow or other head support includes multiple sensors.
Figure 25:
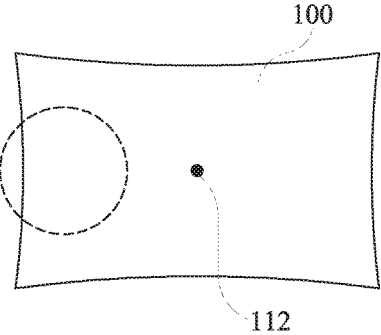
FIG. 25 is schematic plan view of an instrumented pillow and an occupant's head comparing the first method and the related method in terms of their ability to distinguish between the occupant's head being absent from the pillow and the occupant's head being present on the pillow but laterally offset toward one of the lateral edges.

FIG. 24 discloses a related method for monitoring an occupant of the occupant support. The method of FIG. 24, unlike that of FIGS. 17-18, employs a pillow embodiment in which the sensor array 110 includes multiple sensors, for example the three-sensor embodiments of FIGS. 8-10 and 14. At least in an embodiment in which the sensors are weight or other force related sensors, the presence of multiple sensors causes the method to be better than the single sensor method at distinguishing between the occupant's head being absent from the pillow and the occupant's head being present on the pillow but laterally offset toward one of the lateral edges far enough to be out of range of the sensor array. This is illustrated in FIG. 25 which shows an occupant's head (dashed line circle) offset to the right on each of two pillows—one having a single sensor and the other having three laterally distributed sensors. In the case of the single sensor, the sensor reading is zero. As a result, the rules engine is unable to distinguish between the occupant's head being absent from the pillow and the occupant's head being present on the pillow but laterally offset to a location near one of the lateral edges (which is the depicted reality). In the case of three sensors, if sensor 112L reads zero, and sensor 112R reads nonzero (either low or high) the rules engine can determine that the occupant's head is present and offset to the right. If all three readings are zero, the rules engine can determine that the occupant's head is absent from the pillow.

According to the related method, processor 120 receives readings from the sensors at successive points in time and executes instructions from memory 122 to determine the state of the occupant. At block 130 the method acquires the current sensor readings. At block 132 the method updates a temporal record of readings in memory 122 by adding the current readings to the record. The method may also select a set of relevant readings to use in one or more subsequent steps. In one example the set of relevant readings includes all the readings no older than t time units. In another example the set of relevant readings includes the current reading and one or more previous readings without regard for the age of the readings.

The method then proceeds to block 134. Block 134 of FIG. 24, unlike block 134 of FIG. 17 is subdivided into two steps which may be carried out concurrently or in either order. Step 134A establishes a lateral position history, i.e. the history of the lateral position of the occupant's head. The lateral position history reflects the pattern of readings, over time, of sensors which are laterally distributed in one or more rows. If the sensors are weight sensors the lateral position history reflects the pattern of loading and unloading, over time, of sensors which are laterally distributed in one or more rows. Step 134B establishes a vertical position history, i.e. the history of the vertical position of the occupant's head. The vertical position history is determined from the readings from the sensors. If the sensors are weight sensors, the vertical position history is determined from the pattern of loading and unloading of the pillow as revealed by the sum of the readings taken from the sensors at a first time relative to the sum of the sensor readings taken at one or more other times. For example if sensors 112R, 112M and 112L read zero, 10 pounds, and zero respectively at a time $t_i$, read zero, zero and zero at $t_i+\Delta t$ and read 5 pounds, 5 pounds, and zero at time $t_i+2\Delta t$ it may be inferred that the occupant has lifted her head and put it back down on the pillow. Therefore the vertical history record is updated at step 135 to reflect this fact. In this particular example the sensors also provide additional information that the occupant has shifted her head to the right.

The method then proceeds to block 136 where it characterizes the position history which has been developed from the sensor readings. Specifically, the method characterizes the vertical and lateral position histories of the occupant's head. The method as illustrated uses a lookup table stored in memory 122 to carry out the characterization. An example of such a table is the table of FIG. 26, selected cells of which are numbered for ease of reference in the following discussion. The method then proceeds to block 138 where it issues a signal to report the occupant's state. In the example the signal causes video monitor 130 (FIGS. 12-16) to report the state of the occupant.

Returning to block 136 of FIG. 24 and the lookup table of FIG. 26, the table shows a gridwork with two possible patterns of the occupant's lateral head position (columns 1 and 2 below "Lateral Position History") and three possible patterns of the occupant's vertical head position (rows 1, 2 and 3 to the right of "Vertical History"). The lateral position history indicates the history of movement (or lack thereof) of the occupant's head to the left and right on the pillow. The vertical history indicates the history of movement (or lack thereof) of the occupant's head vertically onto and off of the pillow. Each row and column includes a schematic graph to help the reader visualize the movement pattern. The graph of row 1 shows a sustained presence of the occupant's head during the time interval identified by the double headed arrow. The graph of row 2 shows repetitive transitions indicating alternating presence and absence of the occupant's head on the pillow. The graph of row 3 shows a sustained absence of the occupant's head from the pillow during the time interval identified by the double headed arrow. The graph of column 1 (actually three sub-graphs) shows a sustained left lateral position, a sustained central or middle position, and a sustained right lateral position of the occupant's head on the pillow. The graph of column 2 shows a repetitive lateral movement of the occupant's head on the pillow, for example an alternating left/right movement. The reader is referred to FIGS. 19-23 and the accompanying text for a discussion of sustained presence, one-time transitions and repetitive transitions.

If the lateral position history indicates repetitive lateral movement of the occupant's head (col. 2), such as an alternating movement, or the vertical history indicates other than sustained presence of the occupant's head on the head support (rows 2, 3), the method may report that the occupant is in a state other than an acceptable state (cells 2, 3, 4, 5, 6).

The "other than sustained" presence of the occupant's head on the head support may be a sustained absence (row 3; cells 3, 6) or may be a repeated alternation of presence and absence (row 2; cells 2, 5). In the case of the sustained absence of row 3 the method may consider the "other than acceptable" state to be an unacceptable state. This is because the sustained absence of the occupant's head on the head support is consistent with a possible unauthorized egress from the bed (row 3; cells 3, 6). Block 138 may therefore report that the "other than acceptable state" is an unacceptable state and/or a state of possible egress (row 3; cells 3, 6).

In the case of the repetitive transition between presence and absence of the occupant's head on the head support of row 2, the method may also consider the "other than acceptable" state to be an unacceptable state. However because the occupant's head is not constantly absent from the head support, it is not likely that the occupant is attempting an unauthorized egress. If the lateral position history shows that the occupant is at a sustained lateral position (column 1), only one of the histories, in this case the vertical history, involves repetitive movement. Therefore the combination of the sustained lateral position history of column 1 and the alternating presence or absence of the occupant's head on the head support at row 2 (which intersect at cell 2) may be considered to be a mildly unacceptable state. The method therefore may report that the unacceptable state of cell 2 is a mildly unacceptable state. The method may also or instead report an occupant state other than attempted egress.

However if the lateral position history shows that the occupant is undergoing repetitive lateral movement (column 2) both the vertical history and the lateral position history involve repetitive movement. This suggests an occupant state or condition more serious than the sustained lateral position and alternating presence and absence of cell 2, but not as serious as an egress attempt (cells 3, 6). Therefore the combination of the repetitive lateral movement of column 2 and the alternating presence or absence of the occupant's head on the head support at row 2 (which intersect at cell 5) may be considered to be a moderately unacceptable state. The method therefore may report that the unacceptable state of cell 5 is a moderately unacceptable state. The method may also or instead report an occupant state other than attempted egress.

If the lateral position history indicates repetitive lateral movement, and the vertical history indicates sustained presence of the occupant's head on the head support (cell 4) the method may report that the unacceptable state is a mildly unacceptable state. The state of the occupant is considered to be mildly unacceptable because only one of the histories, in this case the lateral history, involves repetitive movement.

If the lateral position history indicates a sustained lateral position of the occupant's head and the vertical history indicates a sustained presence of the occupant's head on the pillow, the method may report that the occupant is in an acceptable state or condition and/or that the occupant is resting (cell 1).

As seen from the foregoing, the content of the report issued at block 138 may depend on both the lateral position history and the vertical position history. Specifically, the content of the report may depend on the intersection of the applicable row with the applicable column. However the principle of intersection does not apply to the intersection of either column with row 3. This is because row 3 corresponds to a condition of sustained absence of the occupant's head from the head support, which is inconsistent with both the sustained lateral position history of column 1 and the repetitive lateral movement history of column 2, both of which are predicated on the presence of the occupant's head on the head support at least part of the time.

In the case of sustained presence (cell 1 of FIG. 26), step 136 may use a lookup table such as table 2 below to refine the content of the report issued at block 138. The lookup table is based on an embodiment in which weight is the sensed parameter.

TABLE 2

| | 1<br>left<br>sensor | 2<br>center<br>sensor | 3<br>right<br>sensor | 4<br>Fault<br>State | 5<br>Remarks |
|---|---|---|---|---|---|
| 1 | H | H | H | FAULT | same nonzero reading from all sensors |
| 2 | H | H | L | FAULT | adjacent nonzero readings the same |

TABLE 2-continued

| | 1<br>left<br>sensor | 2<br>center<br>sensor | 3<br>right<br>sensor | 4<br>Fault<br>State | 5<br>Remarks |
|---|---|---|---|---|---|
| 3 | H | H | Z | FAULT | adjacent nonzero readings the same |
| 4 | H | L | H | FAULT | weight increases in both directions from ctr |
| 5 | H | L | L | FAULT | adjacent nonzero readings the same |
| 6 | H | L | Z | VALID | PRESENT, RESTING, OFFSET LEFT |
| 7 | H | Z | H | FAULT | weight increases in both directions from ctr |
| 8 | H | Z | L | FAULT | weight increases in both directions from ctr |
| 9 | H | Z | Z | VALID | PRESENT, RESTING, OFFSET LEFT |
| 10 | L | H | H | FAULT | adjacent nonzero readings the same |
| 11 | L | H | L | FAULT | implausible symmetry |
| 12 | L | H | Z | VALID | PRESENT, RESTING, OFFSET LEFT |
| 13 | L | L | H | FAULT | adjacent nonzero readings the same |
| 14 | L | L | L | FAULT | same nonzero reading from all sensors |
| 15 | L | L | Z | FAULT | adjacent nonzero readings the same |
| 16 | L | Z | H | FAULT | weight increases in both directions from ctr |
| 17 | L | Z | L | FAULT | weight increases in both directions from ctr |
| 18 | L | Z | Z | VALID | PRESENT, RESTING, OFFSET LEFT |
| 19 | Z | H | H | FAULT | adjacent nonzero readings the same |
| 20 | Z | H | L | VALID | PRESENT, RESTING, OFFSET RIGHT |
| 21 | Z | H | Z | VALID | PRESENT, RESTING, CENTERED |
| 22 | Z | L | H | VALID | PRESENT, RESTING, OFFSET RIGHT |
| 23 | Z | L | L | FAULT | adjacent nonzero readings the same |
| 24 | Z | L | Z | FAULT | implausible symmetry |
| 25 | Z | Z | H | VALID | PRESENT, RESTING, OFFSET RIGHT |
| 26 | Z | Z | L | VALID | PRESENT, RESTING, OFFSET RIGHT |
| 27 | Z | Z | Z | VALID | ABSENT |

In the table, H, L and Z indicate high, low and zero readings from the sensor identified at the top of columns 1-3. Several of the combinations of readings are of suspect validity. Hence, column 4 shows whether or not the set of readings is thought to be valid, but is not intended to exclude other interpretations of the readings. Column 5 includes messages that may be a report or part of a report issued at block 138. The related method, like the first method, reports that the occupant's head is present on the pillow and/or that the occupant is resting. However because of the multiple sensors, the related method offers more certitude as to the direction of any offset as seen in rows 6, 9, 12, 18, 20, and 22. In addition, the readings offer clues as to the magnitude of any offset. For example the readings of both rows 6 and 9 suggest that the occupant is off center to the left. However the two zero readings of row 9 suggest that the occupant is further to the left than is suggested by the low and zero readings of row 6.

Figure 27:
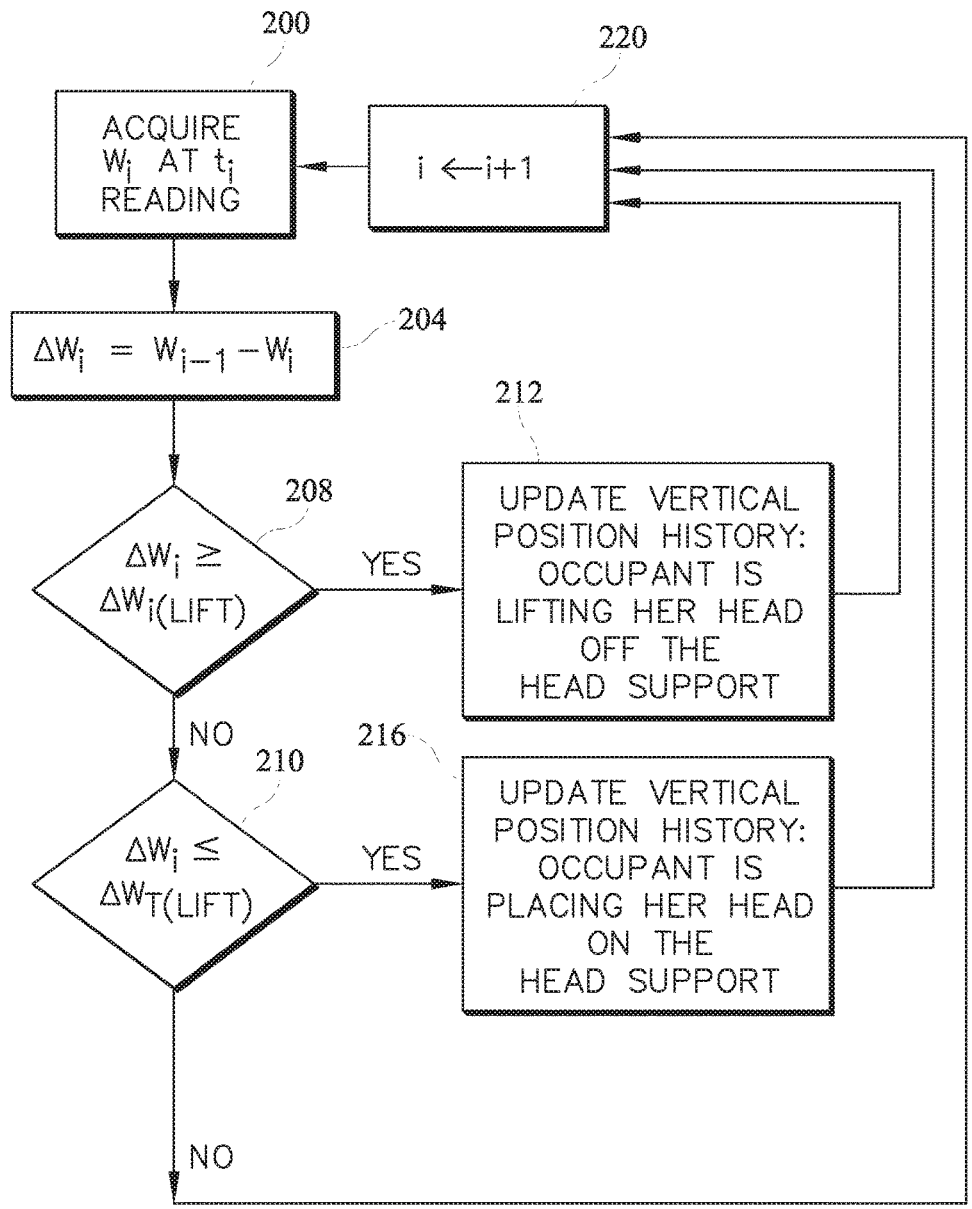
FIG. 27 is a block diagram showing a method for determining if an occupant is lifting her head off a pillow or applying her head to the pillow, for example by applying the weight of her head to the pillow.

FIG. 27 is a block diagram showing a method for establishing the vertical position history of the occupant's head as required at block 134B of FIG. 24. The method exemplified by FIG. 27 is based on an apparatus whose sensors are force related sensors, however the methodology may apply equally well to sensors, and readings therefrom, which are not force related sensors. The method shown in FIG. 27 determines if an occupant is lifting her head off the pillow or applying the weight of her head to the pillow. The method is shown "in progress", i.e. after enough time has elapsed that values are known for all the terms on the right side of the equation at block 204. In the diagram W stands for the sum of the individual weights indicated by weight sensors 112. At block 200 the method acquires weight reading $W_i$ at time $t_i$. At block 204 the method calculates the difference $\Delta W_i$ between weight $W_{i-1}$ at the previous point in time, $t_{i-1}$, and weight $W_i$ at the present point in time, $t_i$. In other words the method determines the difference between a first reading from a sensor (or the sum of the readings from a group of sensors) at a first time and a second reading (or sum of readings) from the same sensor (or group of sensors) at a second time. At block 208 the method compares $\Delta W_i$ to a lifting threshold $\Delta W_{T(LIFT)}$. If the difference $\Delta W_i$ is greater than or equal to the lifting threshold, $\Delta W_{T(LIFT)}$, the method proceeds to block 212 and updates the vertical position history record in memory 122 to indicate that the occupant is lifting (or has lifted) her head off the head support. Otherwise the method proceeeds to block 210 where it tests whether $\Delta W_i$ is less than or equal to $\Delta W_{T(PLACE)}$. If so the method proceeds to block 216 and updates the vertical position history record in memory 122 to indicate that the occupant is placing (or has placed) her head on the head support. Irrespective of whether the procedure follows the YES branch out of block 208, the YES branch out of block 210 or the NO branch out of block 210, the method eventually arrives at block 220 where it increments time subscript i by one. The method then repeats itself with new, later acquired values of $W_i$ and $W_{i-1}$.

The possibility of an equal value is paired with the possibility of "greater than" at block 208 and with the possibility of "less than" at block 210. However the tests at blocks 208, 210 could instead be expressed as pure inequalities. Unless specified otherwise in this specification, and provided no logical inconsistency results, references to possible outcomes of "less than or equal to" and "greater than or equal to" may be interpreted either literally or as pure inequalities. Similarly, references to possible outcomes of "less than" and "greater than" may each be interpreted as including the possibility of equal values, once again provided no logical inconsistency results. One example of a logical inconsistency is a decision block specifying that the method follows a first path if a parameter is less than or equal to a reference value and follows a second path if the parameter is greater than or equal to the reference value. In that case, the pairing of "equal to" with both "greater than" and "less than" is logically inconsistent because if the "equal to" condition were satisfied the path which the method should follow would be indeterminate.

In a specific numerical example, $\Delta W_{T(LIFT)}=4$, $\Delta W_{T(PLACE)}=-5$, $W_{i-1}=9$, and $W_i=3$. At block 204, $\Delta W_i=+6$. At block 208 the $\Delta W_i$ value of +6 is compared to the $\Delta W_{T(LIFT)}$ threshold of +4. Because $\Delta W_i$ is greater than or equal to $\Delta W_{T(LIFT)}$, the method proceeds to block 212, where it updates the vertical position history to show that the occupant is lifting or has lifted her head off the head support. If, at two later times, $W_{i-1}=2$ and $W_i=10$, then at block 204, $\Delta W_i=-8$. At block 208 the $\Delta W_i$ value of $-8$ is compared to the $\Delta W_{T(LIFT)}$ threshold of 4. Because $\Delta W_i$ is not greater than or equal to $\Delta W_{T(LIFT)}$, the method proceeds to block 210. At block 210 the $\Delta W_i$ value of $-8$ is compared to the $\Delta W_{T(PLACE)}$ threshold of $-5$. Because $\Delta W_i$ is less than or equal to $\Delta W_{T(PLACE)}$, the method proceeds to block 216, where it updates the vertical position history to show that the occupant is placing or has placed her head on the head support.

Figure 28:
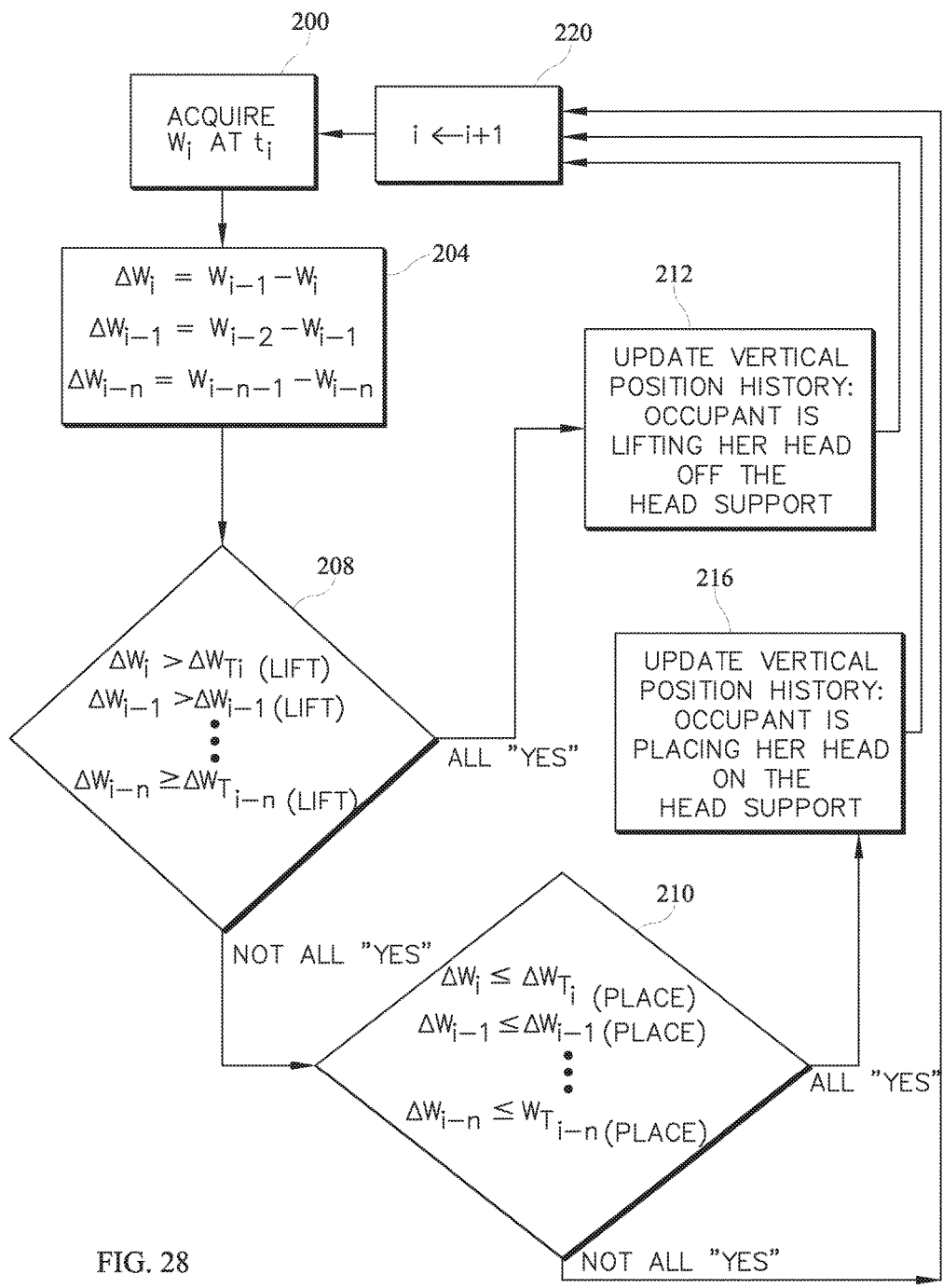
FIG. 28 is a block diagram showing a generalization of the method of FIG. 27.

FIG. 28 shows a generalization of the method of FIG. 27, once again using weight sensors as an example. At block 200 the method acquires readings from a sensor at n points in time thereby establishing a set of n readings $R_1$ through $R_n$ which are stored in memory 122. In FIG. 28, block 204 calculates multiple weight differences between successive pairs of temporally adjacent weight readings. In particular the method determines n−1 differences between successive pairs of temporally adjacent weight readings wherein the kth difference is the difference between $R_{k+1}$ and $R_k$. The differences are calculated for values of k from 1 through n−1. At blocks 208 and 210 the method carries out individual comparisons of each weight difference to a weight difference threshold. The weight difference thresholds may all have the same value or may be customized to each weight difference, as shown. As illustrated, the method proceeds from block 208 to block 212 only if all the weights are greater than or equal to their respective thresholds. Similarly the method proceeds from block 210 to block 216 only if all the weights are less than or equal to their respective thresholds. However other criteria for proceeding from block 208 to 212 or from 210 to 216 may also be satisfactory. For example the criterion may be that only a given proportion of the individual comparisons need to be satisfied in order to proceed from block 208 to 212 or from 210 to 216. In another example some of the individual comparisons may be more heavily weighted than others such that the method can proceed from block 208 to 212 or from 210 to 216 if a relatively small proportion of highly weighted comparisons are satisfied or if a relatively large proportion of less highly weighted comparisons are satisfied. Although the concept of determining differences between pairs of temporally adjacent sensor readings, and the concept of weighting the comparisons, have been described in terms of weight readings, they may apply equally well to readings from sensors which are not force related sensors.

The procedure of FIG. 28 need not acquire, at block 204, all the readings that will be needed at block 208 before beginning the comparisons of block 208. As long as sufficient readings have been acquired at block 204 to carry out at least one of the comparisons of block 208, the method can begin to carry out those comparisons in parallel with the acquisition of additional readings at block 204.

The comparisons at blocks 208 and 210 may be normalized. For example the test at block 208 may be expressed as set forth below:

$$\frac{Q_{i-1} - Q_i}{Q_i} \leq \Delta Q_{T(LIFT)}$$

where Q is a parameter sensed by the instrumentation package, and the $Q_i$ term in the denominator scales parameters having different ranges (e.g. weights versus pressures) or having different orders of magnitude so that threshold $\Delta Q_{T(LIFT)}$ is a threshold applicable to any of those parameters. In effect, the quotient on the left side of the inequality is a percentage change rather than an absolute change.

Figure 29:
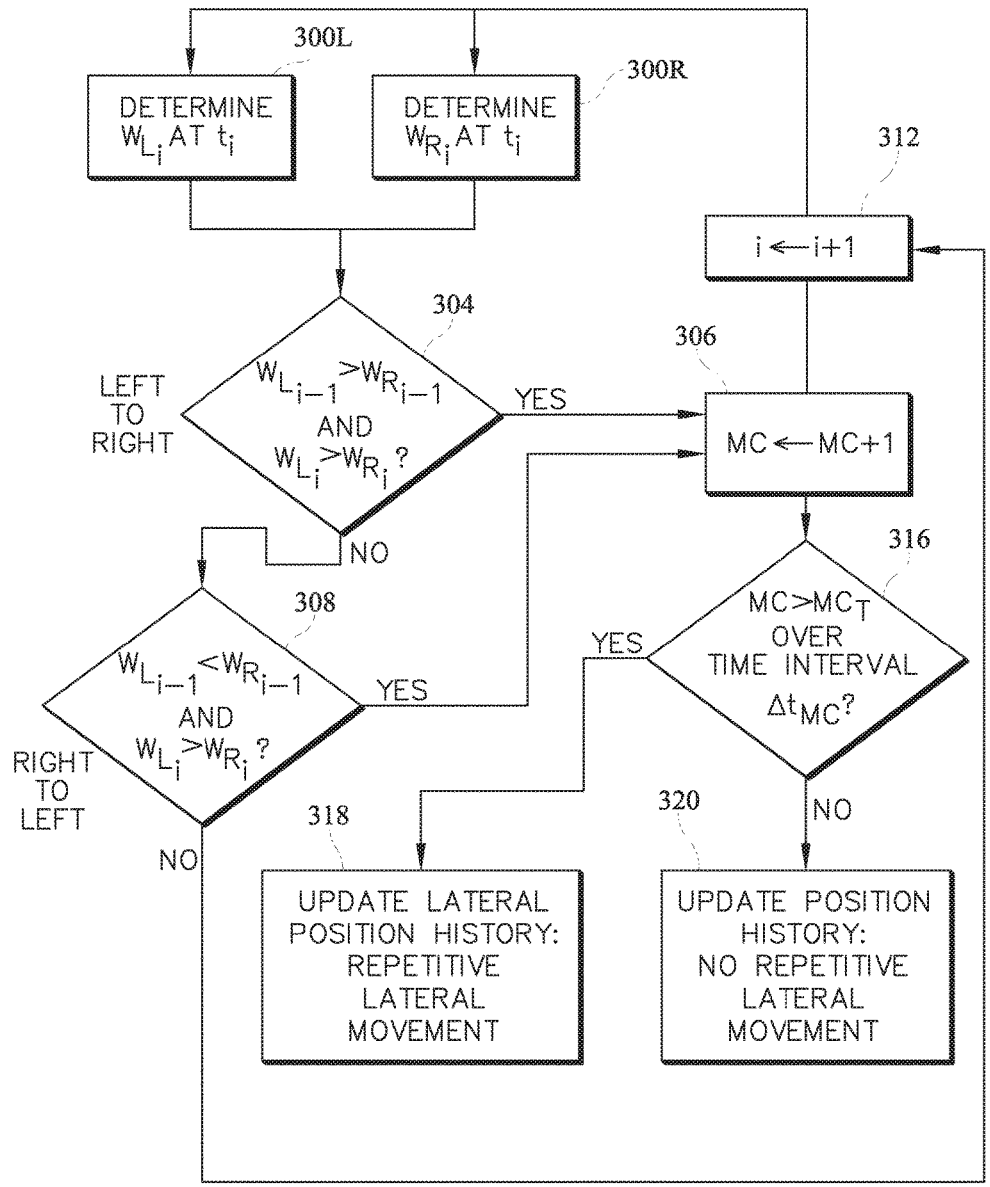
FIG. 29 is a block diagram showing a method for determining if an occupant is moving her head laterally with respect to the pillow, for example by determining if the occupant is moving the weight of her head laterally on the pillow.

FIG. 29 is a block diagram showing a method for establishing the lateral position history of the occupant's head as required at block 134A of FIG. 24. The method of FIG. 29 determines if an occupant is moving her head laterally on the pillow, for example by translating her head or rocking her head. The method as diagramed is based on a pillow with two laterally spaced apart weight sensors 112, such as left sensor 112L and right sensor 112R shown in FIG. 12. $W_L$ and $W_R$ are the readings from the left and right sensors. The method is shown "in progress", i.e. after enough time has elapsed that values are known for all the terms on the right side of the inequalities at blocks 304 and 308.

At blocks 300L and 300R the method acquires weight reading $W_{Li}$ and $W_{Ri}$ from the left and right sensors 112L, 112R at time $t_i$. At block 304 the method compares the previous values of the left and right weight readings to each other and compares the current values of the left and right weight readings $W_{Li-1}$, $W_{Ri-1}$ to each other. If the comparison shows that the past value of the left weight reading exceeded the past value of the right weight reading ($W_{Li-1} > W_{Ri-1}$) and the present value of the left weight reading is less than the present value of the right weight reading ($W_{Li} < W_{Ri}$), the method recognizes that weight has shifted left to right and therefore the method proceeds to block 306 where it increments a movement counter MC by one. However if the comparison at block 304 shows that the past value of the left weight reading did not exceed the past value of the right weight reading or that the present value of the left weight reading is not less than the present value of the right weight reading, the method proceeds to block 308. At block 308 the method once again compares the previous values of the two weight readings to each other and compares the current values of the two weight readings to each other. If the comparison shows that the past value of the left weight reading was less than the past value of the right weight reading ($W_{Li-1} < W_{Ri-1}$) and the present value of the left weight reading is greater than the present value of the right weight reading ($W_{Li} > W_{Ri}$), the method recognizes that weight has shifted right to left and therefore the method proceeds to block 306 where it increments the movement counter MC by one. If the test at block 308 is not satisfied the method proceeds from block 308 to block 312 where it increments time subscript i by one. The method then proceeds to blocks 300L and 300R and begins a new cycle.

If the test at block 304 or the test at block 308 is satisfied, the method increments the motion counter MC at block 306. The method then proceeds to both block 312 to begin a new cycle and to block 316. At block 316 the method tests if a motion count, as indicated by the value of motion counter MC, has exceeded a motion count threshold $MC_T$ during a specified interval of time $\Delta t_{MC}$. If so, the method proceeds to block 318 where it updates the lateral position history to indicate that the occupant is undergoing sustained lateral movement. Additionally or alternatively the report may offer an interpretation of the sustained lateral movement, for example by advising that the occupant is uncomfortable or restless. However if block 316 reveals that the value of the motion counter MC, has not exceeded the motion count threshold $MC_T$ during a specified interval of time $\Delta t_{MC}$, the method proceeds to block 320. At block 320 the method may update the lateral position history consistent with the observation that no sustained lateral movement has been detected.

Figure 30:
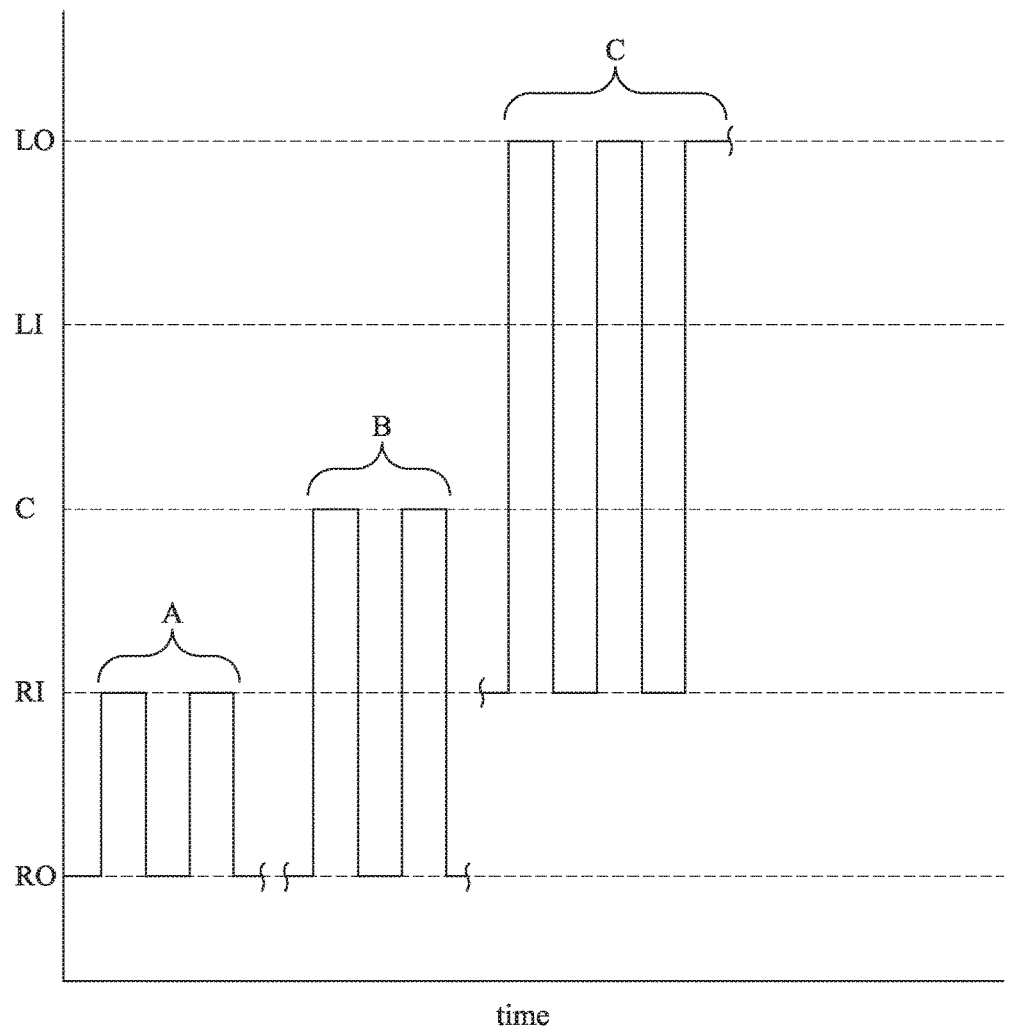
FIG. 30 is a graph useful for understanding an adaptation of the method of FIG. 29.

Referring to FIG. 30, the method of FIG. 29 can be adapted to three or more laterally distributed sensors such as the five sensor configuration of FIG. 15. FIG. 30 shows a graph of example readings from left outboard, left inboard, center, right inboard and right outboard sensors. The adapted method accounts for which sensors are involved in incrementing a motion counter. The repetitive, lateral shift of the weight of the occupant's head on the pillow embraced by brackets A, B and C occur over different distances. Information about the spatial extent of the weight shifts may be reported in a report such as that of block 318 of FIG. 29. Additionally or alternatively the method may offer differing interpretations, for example interpreting weight shift C as occupant discomfort and interpreting weight shift A as minor restlessness.

Figure 31:
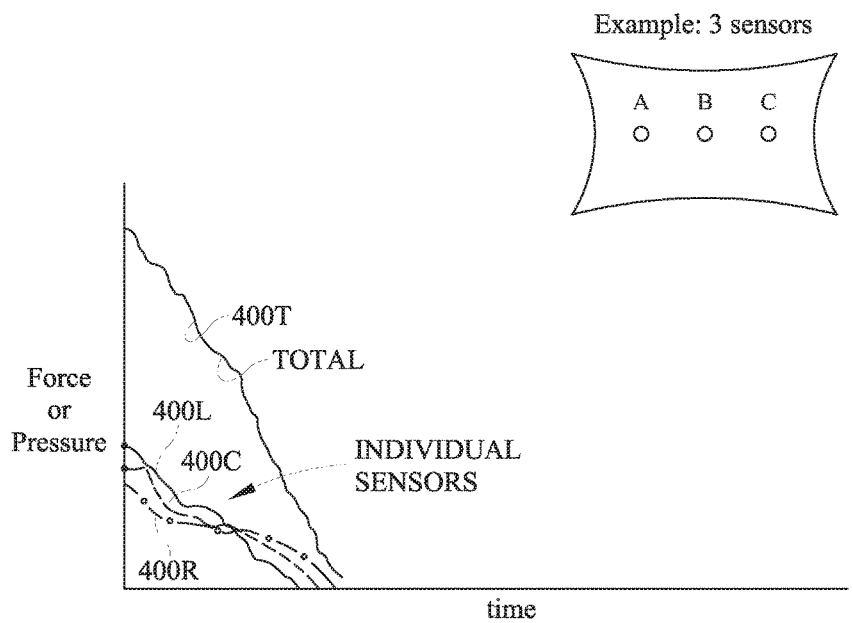
FIGS. 31-32 are graphs illustrating a way that multiple laterally distributed sensors may be used to distinguish between an occupant lifting the weight of her head from the pillow (or applying the weight of her head to the pillow) and moving her head laterally.
Figure 32:
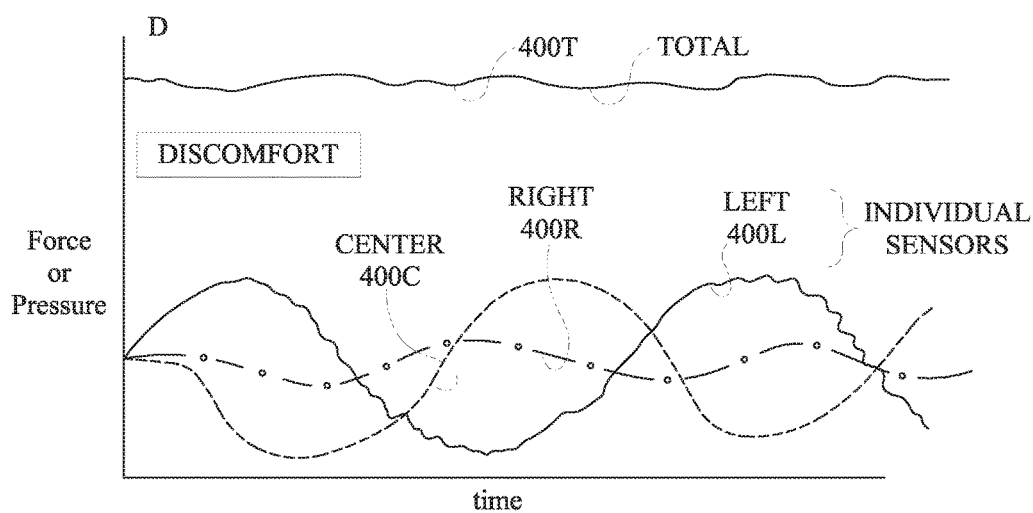

FIGS. 31-32 illustrate another way that multiple laterally distributed sensors 112 may be used to distinguish between an occupant lifting the weight of her head from the pillow (or applying the weight of her head to the pillow) and moving her head laterally. The example of FIGS. 31-32 is based on a three-sensor configuration as shown in FIG. 14 and assumes that the weight of the occupant's head, when resting on the pillow, is approximately equally distributed among all three sensors.

FIG. 31 corresponds to the occupant lifting her head from the pillow. Both the total weight 400T registered by all three sensors and the weight 400L, 400C, 400R registered by each of the individual sensors decreases over time. In general, individual sensors that were not reading zero will go to zero, will all achieve zero at about the same time, and, upon reaching zero, will remain at zero. The total weight reading 400T will also go to zero, will achieve zero at about the same time as the individual weight readings achieve zero, and, upon reaching zero, will remain at zero. The event will also conclude relatively quickly.

FIG. 32 corresponds to the occupant moving her head laterally on the pillow. At least one sensor will produce an oscillatory reading or other time varying reading. If more than one sensor produces an oscillatory reading those readings will be out of phase. The total reading 400T may remain relatively constant as shown in FIG. 32, or, if the spatial extent of the occupant's head movement takes her head outside the spatial range of one or more sensors, the total reading may also change. However either way the total reading 400T is not expected to go to zero. The event is sustained over time, unlike that of FIG. 31 which concludes quickly. If and when the occupant stops moving her head laterally the total force reading 400T will be other than zero, and at least one of the sensors will also produce a reading other than zero.

Figure 33:
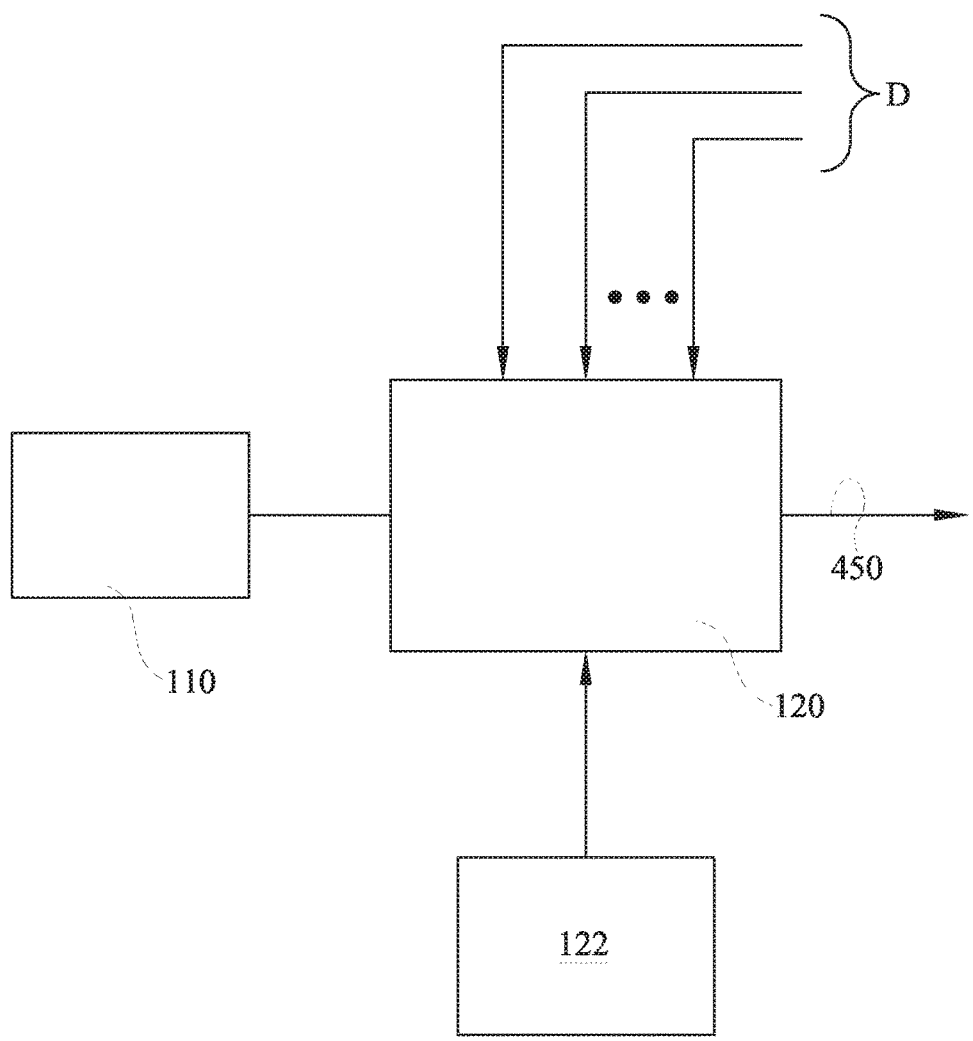
FIG. 33 is a magnified view of a processor, sensor array, and memory to demonstrate the use of information from sources other than the sensors of the instrumentation package to monitor and assess the status of an occupant.

Referring to FIGS. 33-34, information from sources other than the sensors 112 of the head support 100 or 102 can also be used to monitor occupant status. FIG. 33 is a magnified view of elements visible in other illustrations, namely processor 120, sensor array 110, and memory 122. The processor receives information from sensor array 110 and processes that information to assess the spatial and temporal relationship of the occupant's head relative to the pillow. Among these relationships are whether or not the occupant's head is resting on the pillow, where the occupant's head is positioned relative to one or more datums such as centerlines 104, 106 or edges 90, 92, 94, 96, and the history of any changes in the position of the occupant's head. The processor also receives data D from one or more other sources. These other sources may include data from a PPM system and data from sensors indicating siderail position (stowed or deployed). The processor produces an occupant status report 450 which depends on both the data from sensor array 110 and the data D from the other source or sources. The integration of the sensor array data and the other data may be accomplished by a lookup table. An example lookup table is shown in FIG. 34, selected cells of which are numbered for easy reference in the following description.

The example lookup table of FIG. 34 considers the vertical and lateral position history of the occupant's head as determined from sensor array 110 (rows 1-5) as well as data from other sensors and systems (columns 1-4). These other systems and sensors include a PPM monitoring system (column 1), sensors to monitor the position of the head and foot siderails (columns 2-3), and sensors that monitor the elevation of the bed, e.g. the distance E from the floor to the elevatable frame as seen in FIG. 1 (col. 4). The entry immediately beneath each column heading shows the condition of the system or sensor listed in the column heading. Each cell includes risk assessment corresponding to the lateral or vertical position history and the condition of the system or sensor named in the column heading. As seen in the lookup table if the other system is a patient position monitoring system, the report arising from cell 2, 3 or 5 is a more elevated risk assessment and the report arising from cell 1 or 4 is a less elevated risk assessment.

The risk assessments shown in FIG. 34 may account for both risk severity and the severity of the consequences. For example the Medium-High risk at cell 18 reflects the possibility that a sustained absence of the occupant's head from the pillow (row 3) indicates that the occupant may be intent on exiting the bed and that exiting a bed which is not at its lowest elevation (column 4) may have more severe consequences than exiting a bed which is at its lowest elevation.

Each example risk assessment of FIG. 34 is based on a single class of occupant position history, i.e. a vertical history or lateral history, but not both, and on one other parameter. However risk assessments can be based on multiple classes of occupant position history (e.g. accounting for both vertical and lateral history) and/or on multiple other parameters taken collectively.

Although this disclosure refers to specific embodiments, it will be understood by those skilled in the art that various changes in form and detail may be made without departing from the subject matter set forth in the accompanying claims. For example, one described feature of the method and apparatus disclosed herein is the head support portion which can be a pillow 100, a head support portion of a mattress 102 or can take some other form. A second feature is the architecture of the monitoring package which can be entirely on-board the head support or partially off-board. The monitoring package can include one or multiple processors, and one or multiple memories. Certain instructions stored in memory can be physically or notionally divided into a rules engine RE and a decision engine DE, or not. A third feature is the quantity and distribution of sensors. A fourth feature is the use of the vertical position history standing alone, use of the lateral position history standing alone, or combined use of the histories. A fifth feature is the use, or not, of data from sources other than the instrumented head support. The various choices relating to the first three features can be intermixed as desired. Whatever arrangement of the first three features is chosen, that arrangement can be used to carry out a method involving either of the position histories standing alone or involving the combined position histories, subject to the constraint that, as disclosed above, a single sensor is not well suited to assessing the lateral position history. Moreover a method involving any of these position history choices can be extended, or not, to include data from other sources.

In addition, the vertical and horizontal position of the occupant's head may be monitored by a sensing technology which is not on-board the head support, for example by video monitoring. Moreover, some sensing technologies which enable the vertical and horizontal position of the occupant's head to be determined relative to a reference other than a pillow may also be employed.

I claim:

1. A method of monitoring an occupant of an occupant support comprising:
   establishing a lateral position history of the occupant, the lateral position history comprising an assessment of how frequently the occupant's head undergoes a lateral transition relative to a head support;
   establishing a vertical position history of the occupant, wherein the vertical history accounts for how frequently the occupant's head is applied to and removed from the head support; and
   if the lateral position history indicates sustained repetitive lateral movement or the vertical history indicates other than sustained presence of the occupant's head on the head support, reporting that the occupant is in a state other than an acceptable state.

2. The method of claim 1 wherein if the vertical history indicates sustained absence of the occupant's head from the head support, reporting at least one of an unacceptable state and a state of possible egress.

3. The method of claim 1 wherein if the vertical history indicates alternating presence and absence of the occupant's head on the head support, reporting that the occupant is in an unacceptable state.

4. The method of claim 3 wherein if the lateral position history indicates a sustained lateral position of the occupant's head, reporting that the unacceptable state is one of a mildly unacceptable state and a state other than a possible egress state.

5. The method of claim 3 wherein if the lateral position history indicates alternating lateral movement, reporting that the unacceptable state is one of a moderately unacceptable state and a state other than a possible egress state.

6. The method of claim 1 wherein if the lateral position history indicates alternating lateral movement, and the vertical history indicates sustained presence of the occupant's head on the head support, reporting that the occupant is in an unacceptable state.

7. The method of claim 6 wherein the reported unacceptable state is one of a mildly unacceptable state and a state other than a possible egress state.

8. The method of claim 1 wherein if the lateral position history indicates a sustained lateral position of the occupant's head and the vertical history indicates sustained presence of the occupant's head on the head support, reporting that the occupant is in one of an acceptable state and a resting state.

9. The method of claim 1 wherein the step of establishing the vertical position history comprises:
   determining the difference between a first reading from a sensor at a first time and a second reading from the sensor at a second time; and
   if the difference is greater than a lifting threshold, updating the vertical position history to reflect lifting of the occupant's head from the head support; and
   if the difference is less than or equal to a placement threshold updating the vertical position history to reflect placement of the occupant's head on the head.

10. The method of claim 1 wherein the step of establishing the vertical position history comprises:
    acquiring a reading from a sensor at n points in time thereby establishing a set of readings $R_1$ through $R_n$;

determining n−1 differences between successive pairs of temporally adjacent readings wherein the kth difference is the difference between $R_k$ and $R_{k-1}$ for k equal to 1 through n−1;

comparing each difference to a difference threshold.

11. The method of claim 1 wherein the step of establishing the lateral position history comprises:

acquiring, at a time $t_{i-1}$, a reading $W_{Li-1}$ from a first sensor and a reading $W_{Ri-1}$ from a different sensor which is spaced from the first sensor;

acquiring, at a time $t_i$, a reading $W_{Li}$ from the first sensor and a reading $W_{Ri}$ from the different sensor which is spaced from the first sensor; and if $(W_{Li-1}>W_{Ri-1}$ AND $W_{Li}<W_{Ri})$ OR $(W_{Li-1}<W_{Ri-1}$ AND $W_{Li}>W_{Ri})$, incrementing a counter MC.

12. The method of claim 11 including updating the lateral position history if MC>$MC_T$ over a time interval $\Delta t_{MC}$.

13. The method of claim 1 wherein the step of establishing a lateral position history of the occupant and the step of establishing a vertical position history of the occupant rely on a sensor reading, and at least one of the step of establishing a lateral position history and the step of establishing a vertical position history distinguishes among a sustained sensor reading, a one-time transient reading, and a repetitive transient reading.

14. The method of claim 13 wherein:

a sustained reading is one that has remained substantially constant for at least a prescribed number of time units;

a one-time transient is identified by a transition from a first value to a second value without an oppositely directed transition occurring in a specified number of time units following the transition from the first value to the second value; and a repetitive transient is identified by a specified number of oppositely directed transitions occurring within a time window of no more than a designated number of time units.

15. The method of claim 13 wherein the sensor reading is of a force related parameter.

16. A method of monitoring an occupant of an occupant support having a head support with at least one sensor which senses a parameter associated with the head support, the method comprising:

establishing a spatial and temporal relationship of the occupant's head relative to the head support based on information acquired from the at least one sensor;

acquiring information from at least one source other than the head support;

producing an occupant status report which depends on the spatial and temporal relationship and on the information from the at least one other source.

17. The method of claim 16 wherein the at least one other source includes a patient position monitoring system.

18. The method of claim 16 wherein:

the method reports a risk assessment;

the step of establishing a spatial and temporal relationship includes establishing a vertical position history of the occupant's head and establishing a lateral position history of the occupant's head;

if the vertical position history indicates a repetitive presence and absence or indicates a sustained absence or if the lateral position history indicates a repetitive lateral movement, the risk assessment is more elevated risk assessment; and if the vertical position history indicates a sustained presence or the lateral position history indicates a sustained lateral position, the risk assessment is a less elevated risk assessment.

19. A head support comprising:

a monitoring package associated with the head support, the monitoring package comprising an instrumentation package, a processor and a memory, the instrumentation package including at least one sensor, the processor adapted to execute instructions which:

establish a relationship of a person's head relative to the head support based on information acquired from the at least one sensor; and produce a report of the person's state based on the relationship.

20. The head support of claim 19 comprising at least two laterally distributed sensors.

21. The head support of claim 19 wherein the instrumentation package, the processor and the memory are on-board components.

22. The head support of claim 19 wherein the processor receives information from at least one source other than the head support, and the report produced by the processor is based on the information from the at least one other source.

23. The head support of claim 19 wherein the sensor senses a force related parameter.

* * * * *